United States Patent [19]
Baumann et al.

[11] Patent Number: 5,698,449
[45] Date of Patent: Dec. 16, 1997

[54] SYNTHETIC PEPTIDE AND ITS USES

[75] Inventors: Michael A. Baumann, Baltimore, Md.; Byron E. Anderson, Morton Grove, Ill.

[73] Assignee: Northwestern University, Evanston, Ill.

[21] Appl. No.: 335,049

[22] Filed: Nov. 7, 1994

Related U.S. Application Data

[62] Division of Ser. No. 598,416, Oct. 16, 1990, Pat. No. 5,364,930.

[51] Int. Cl.$^6$ .................................................. G01N 33/564
[52] U.S. Cl. .................... 436/507; 436/518; 436/538; 436/807; 514/14; 530/326; 530/327; 530/413
[58] Field of Search .................... 436/507, 535, 436/538, 541, 539, 518, 807; 514/12, 13, 14, 15; 530/326, 327, 328, 413, 415

[56] References Cited

U.S. PATENT DOCUMENTS

| | | | |
|---|---|---|---|
| 3,941,763 | 3/1976 | Sarantakis | 260/112.5 |
| 4,546,082 | 10/1985 | Kurjan et al. | 435/172.3 |
| 4,588,684 | 5/1986 | Brake | 435/68 |
| 4,775,622 | 10/1988 | Hitzeman et al. | 435/68 |
| 4,945,039 | 7/1990 | Suzuki et al. | 435/7 |
| 5,084,398 | 1/1992 | Huston et al. | 436/535 |
| 5,364,930 | 11/1994 | Baumann et al. | 530/326 |

OTHER PUBLICATIONS

Blair, A.H., and Ghose, T.I., *J. Immunol. Methods*, 59:129–143 (1983).
Burton, *Molec. Immunol.*, 22, 161–206 (1985).
Burton, *Molec. Immunol.*, 25, 1175–81 (1988).
Burton et al., *Nature*, 288, 338–44 (1980).
Chou and Fasman, *Adv. Enzym.*, 47, 45–148 (1978).
Davis et al., *Biochem. Int'l.*, 10, 395–404 (1985).
DeGrado et al., *J. Am. Chem. Soc.*, 103, 679–81 (1981).
Duncan and Winter, *Nature*, 332, 738–40 (1988).
Ellman, *Arch. Biochem. Biophys.*, 74, 443–450 (1958).
Ellman, *Arch. Biochem. Biophys.*, 82, 70–77 (1959).
Fields, *Meth. Enzymol.*, 25B, 464–68 (1972).
Garnier et al., *J. Molec. Biol.*, 120, 97–120 (1978).
Gauthier et al., *J. Exp. Med.*, 156:766–777 (1982).
Geusdon et al., *J. Histochem. Cytochem.*, 27, 1131–39 (1979).
Hughes–Jones and Gardner, *Immunology*, 34, 459–63 (1978).
Jones et al., *J. Immunol. Meth.*, 53, 201–208 (1982).
Kulkarni, P.N., Blair, A.H., and Ghose, T.I., *Cancer Res.*, 41:2700–06 (1981).
Lancet et al., *Biochem. Biophys. Res. Commun.*, 85, 608–614 (1978).
Langone et al., *Adv. Immunol.*, 32, 157–252 (1982).
Langone et al., *J. Immunol.*, 121, 327–32 (1978).
Lukas et al., *J. Immunol.*, 127, 2555–60 (1981).
Marquart et al., *J. Mol. Biol.*, 141, 369–91 (1980).
Merrifield, *J. Am. Chem. Soc.*, 85, 2149–54 (1963).
Moe and Kaiser, *Biochem.*, 24, 1971–76 (1985).
Prystowsky et al., *Biochemistry*, 20, 6349–56 (1981).
Reid, *Biochemical J.*, 179, 367–71 (1979).
Reid et al., *Biochemical J.*, 203, 559–69 (1982).
Stalinheim et al., *Immunochem.*, 10, 501–507 (1973).
Taylor et al., *Mol. Pharmacol.*, 22, 657–66 (1982).
Theofilopoulos and Dixon, *Adv. Immunol.*, 28, 89–220 (1979).
Baumann and Anderson, *J. Biol. Chem.*, 265, 18414 (Oct. 25, 1990).
Veerhuis et al., *Eur. J. Immunol.*, 15, 881–887 (1985).
Endo et al., "An Enzyme–Linked Immunoassay for the Measurement of Circulating Immune Complexes," Ann. Clin. Biochem. (1983) 20:163–168.
Marqués et al., "Arginine Residues of the Globular Regions of Human C1q Involved in the Interaction with Immunoglobulin G," J. Biol. Chem. (1993) 268:10393–02.
Sellar et al., "Characterization and Organization of the Genes Encoding the A–,B–and C–chains of Human Subcomponent C1q," Biochem. J. (1991) 74:481–490.
Comis et al, "Evidence for Arginine Residues in the Immunoglobulin–binding Sites of Humans C1q", Biochim. Biophys. Acta, 842(1):45–51, 1985.

*Primary Examiner*—Carol A. Spiegel
*Attorney, Agent, or Firm*—Sheridan Ross

[57] ABSTRACT

The invention provides a fragment of C1q which is characterized in that a plurality of such fragments selectively binds immune complexes or aggregated immunoglobulins in the presence of monomeric immunoglobulin. The invention also provides a synthetic peptide comprising the sequence:

Leu Glu Gln Gly Glu Asn Val Phe Leu Gln Ala Thr   [SEQ ID NO 2]
 1           5               10 or variants thereof capable of binding immunoglobulin. Like the C1q fragment, a plurality of the peptides can selectively bind immune complexes or aggregated immunoglobulins in the presence of monomeric immunoglobulin. As a result of this property, the fragments and peptides are well-adapted for removing immune complexes and aggregated immunoglobulins from fluids containing monomeric immunoglobulin, and for detecting or quantitating immune complexes in such fluids. The invention also provides a binding material for removing immune complexes or aggregated immunoglobulins from a fluid. The binding material comprises plural binding peptides, the peptides being characterized in that a plurality of them selectively binds immune complexes and aggregated immunoglobulins in the presence of monomeric immunoglobulin.

6 Claims, 15 Drawing Sheets

FIG. 1

PROTEIN A FRAGMENT B
(RESIDUES 142-153):

Asn Glu Glu Gln Arg Asn Gly
1        4   5

Phe Ile Gln Ser Leu
         10

[SEQ ID NO. 1]

C1q B CHAIN HELIX
(RESIDUES 189-200):

Leu Glu Gln Gly Glu Asn
1            5

Val Phe Leu Gln Ala Thr
         10

[SEQ ID NO. 2]

CBP2:

Leu Glu Gln Gly Glu Asn
1            5

Val Phe Leu Gln Ala Thr
         10

Leu Leu Cys
         15

[SEQ ID NO. 3]

B. Protein A Fragment B
(Residues 142-153)

C1q B Chain Helix:
(Residues 189-200)

CBP2

|||||||| Hydrophobic

≡ Moderately Polar

⋯ Hydrophilic

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 12 amino acids
    ( B ) TYPE: amino acid
    ( C ) STRANDEDNESS:
    ( D ) TOPOLOGY: unknown ( x i ) SEQUENCE DESCRIPTION: SEQ ID NO:1:

Asn Glu Glu Gln Arg Asn Gly Phe Ile Gln Ser Leu
                  5                   10

( 2 ) INFORMATION FOR SEQ ID NO:2:

( i ) SEQUENCE CHARACTERISTICS:
    ( A ) LENGTH: 12 amino acids
    ( B ) TYPE: amino acid
    ( C ) STRANDEDNESS:
    ( D ) TOPOLOGY: unknown ( x i ) SEQUENCE DESCRIPTION: SEQ ID NO:2:

Leu Glu Gln Gly Glu Asn Val Phe Leu Gln Ala Thr
                  5                   10

( 2 ) INFORMATION FOR SEQ ID NO:3:

( i ) SEQUENCE CHARACTERISTICS:
    ( A ) LENGTH: 15 amino acids
    ( B ) TYPE: amino acid
    ( C ) STRANDEDNESS:
    ( D ) TOPOLOGY: unknown ( x i ) SEQUENCE DESCRIPTION: SEQ ID NO:3:

Leu Glu Gln Gly Glu Asn Val Phe Leu Gln Ala Thr Leu Leu Cys
                  5                   10                  15

SYNTHETIC PEPTIDE AND ITS USES

This application is a division of application Ser. No. 07/598,416, filed Oct. 16, 1990, now U.S. Pat. No. 5,364,930.

FIELD OF THE INVENTION

This invention relates to a fragment of C1q and to a synthetic peptide and to their use to selectively bind immune complexes and aggregated immunoglobulins. The invention also relates to a binding material which can be used to selectively remove immune complexes and aggregated immunoglobulins from fluids.

BACKGROUND OF THE INVENTION

An immune complex is an aggregate of immunoglobulins, non-immunoglobulin serum proteins, and antigens. Immune complexes are formed as a natural consequence of the immune response to antigens of infectious agents, to normal tissue components in the case of autoimmune diseases, to tumor-associated antigens, and to other antigens. The complexes are normally removed by the cells of the reticuloendothelial system. When this system is compromised or overloaded, circulating immune complexes may deposit in a number of organs, thereby causing possibly severe clinical problems. Further, in cancer, it is postulated that immune complexes may block other effector mechanisms of the immune system which would otherwise destroy malignant cells. Several studies have indicated that removal of circulating immune complexes may be an effective therapeutic technique. See, e.g., Theofilopoulos and Dixon, *Adv. Immunol.*, 28, 90–220 (1979); Theofilopoulos and Dixon, *Immunodiagnostics of Cancer*, page 896 (M. Decker Inc., New York, N.Y. 1979).

Immune complexes form as a result of immunoglobulins reacting with antigens. Immunoglobulins are able to cross-link antigens so that a lattice network of immunoglobulins bound to antigens is formed. Once the antigen-immunoglobulin reaction has occurred, the immune complex can then be decorated with a variety of serum proteins such as the proteins of the complement cascade.

Complement component C1q selectively binds immune complexes in the presence of monomeric immunoglobulin because of the molecule's ability to develop a "functional affinity" when binding immune complexes. A "functional affinity" results when multiple low affinity receptors, confined in space, interact with multiple ligands, which are also confined in space. Normally, an individual ligand would rapidly associate and dissociate from the low affinity receptor but, when multiple ligands in a complex interact with multiple receptors, the dissociation from the receptors is very slow since the probability of all ligands dissociating at the same time is very low. The slower dissociation rate results in an affinity several orders of magnitude greater than the individual receptor's affinity. The difference in affinities for the individual ligand and the complexed ligand produces a selection for the complexed ligand when presented with both species.

The mature C1q molecule contains two distinct portions, the stalk and the globular head. There are six globular head regions per C1q molecule. Each contains a low affinity immunoglobulin binding site. Hughes-Jones and Gardner, *Immunology*, 34, 459–63 (1978); Duncan and Winter, *Nature*, 332, 738–40 (1988). Since there are six globular head regions on C1q, the molecule can form multiple binding interactions with the multiple immunoglobulins present in immune complexes. Id. The result is a higher net affinity for immune complexes (id.) due to the low probability of more than one bound globular head receptor dissociating simultaneously (i.e., a functional affinity develops). Thus, when C1q is presented with both immune complexes and monomeric immunoglobulin, it selectively binds to the immune complexes because of the slower dissociation kinetics of the immune complexes.

Many investigators have tried to identify the residues on immunoglobulins that are recognized by C1q. Initial theoretical studies that compared the sequences of immunoglobulin Fc regions of various species known to bind human C1q produced four possible sites in two general locations: 1) the residues flanking Trp277 and Tyr278 (residues 275–295) (Lukas et al., *J. Immunol.*, 127, 2555–60 (1981); Prystowsky et al., *Biochemistry*, 20, 6349–56 (1981)); and 2) the residues flanking Glu318 (residues 316–338) (Stalinhelm et al., *Immunochem.*, 10, 501–507 (1973); Burton et al., *Nature*, 288, 338–44 (1980)). Various studies by authors advocating one or the other site produced conflicting results.

However, Duncan and Winter recently performed a series of more conclusive experiments. Duncan and Winter, *Nature*, 332, 738–40 (1988). Using recombinant DNA techniques, they were able to systematically alter the various residues of the two disputed sites. Then, by determining the ability to bind C1q of each of the resulting immunoglobulins, the actual site and specific binding residues were determined. They localized the core of the C1q interactions to residues 318, 320, and 322 in the Fc region of human IgG. Despite, the success of Duncan and Winter, the site on immunoglobulins where C1q binds may not be limited to the residues indicated by their work. In fact, other immunoglobulin residues may also be involved in the C1q-immunoglobulin interaction that could not be detected using their approach. This will not be resolved until high resolution x-ray diffraction data are obtained for the C1q-Fc region complex and the complete binding interaction is determined.

Bacterial proteins such as *Staphylococcus aureus* Protein A also bind to the immunoglobulin Fc region. Unlike C1q, the Protein A-immunoglobulin interaction is understood in detail. In a series of crystallographic studies by Deisenhofer, et al., the structure of human IgG Fc, Protein A, and finally the IgG Fc-Protein A Fragment B co-crystal were determined. Deisenhofer et al., *Hoppe-Seyler's Z. Physiol. Chem. Bd.*, 359, S. 975–85 (1978); Marquart et al., *J. Mol. Biol.*, 141, 369–91 (1980). One of the most important pieces of information to come from this structure is the exact contact residues involved in the interaction. Those residues are Met 252, Ile 253, Ser 254, Val 308, Leu 309, His 310, Gln 311, Asn 312, His 433, Asn 434, His 435, and Tyr 436 of the human IgG Fc region. These residues are located at the interface between the CH2 and CH3 regions of the Fc portion of IgG, and some of them (309–312) are in close proximity to the proposed immunoglobulin binding site for C1q (318, 320 and 322).

Unlike C1q, Protein A binds to the Fc portion of immunoglobulins with high affinity. Ellman, *Arch. Biochem. Biophys.*, 74, 443–450 (1958). Thus, Protein A cannot differentiate between complexed and monomeric immunoglobulins.

However, PCT application WO 89/04675 teaches the preparation of analogs of Protein A that have a lower affinity for the Fc region and which can develop a functional affinity for immune complexes when arrayed in a specific manner. The analogs are analogs of a binding domain of Protein A or of related sequences from functionally similar bacterial proteins such as Protein G (see page 10). This PCT application reports that oligomers of the analogs, or an array of the analogs disposed about the surface of an insoluble matrix, develop a functional affinity for immune complexes.

SUMMARY OF THE INVENTION

The invention provides a fragment of C1q which is characterized in that a plurality of such fragments selectively binds immune complexes or aggregated immunoglobulins in the presence of monomeric immunoglobulin. The fragment can be used to bind immune complexes or aggregated immunoglobulins. It can also be used to detect or quantitate immune complexes or to remove immune complexes or aggregated immunoglobulins from fluids. In particular, since a plurality of the fragments can selectively bind immune complexes or aggregated immunoglobulins in the presence of monomeric immunoglobulin, the fragment is especially well-adapted for removing immune complexes and aggregated immunoglobulin from fluids containing monomeric immunoglobulin and for detecting or quantitating immune complexes in such fluids.

The invention also provides a synthetic peptide comprising the sequence:

Leu Glu Gln Gly Glu Asn Val Phe Leu Gln Ala Thr [SEQ ID NO 2]
1           5                        10 or variants thereof capable of binding immunoglobulin. The synthetic peptide can be used to bind immune complexes or aggregated immunoglobulins, to detect or quantitate immune complexes, or to remove immune complexes or aggregated immunoglobulins from fluids. Like the C1q fragment, a plurality of the peptides can selectively bind immune complexes or aggregated immunoglobulins in the presence of monomeric immunoglobulin. As a result of this property, the peptides of the invention are also well-adapted for removing immune complexes and aggregated immunoglobulin from fluids containing monomeric immunoglobulin, and for detecting or quantitating immune complexes in such fluids.

The C1q fragment and the synthetic peptide can be prepared in a number of ways, including using recombinant DNA techniques. Accordingly, the invention also comprises a DNA molecule encoding the C1q fragment or the synthetic peptide, a vector comprising the DNA molecule operatively linked to expression control sequences, and a host cell transformed with the vector. The C1q fragment or synthetic peptide can be prepared by culturing the transformed host cell.

The invention further provides a test kit for detecting or quantitating immune complexes comprising a container of the C1q fragment or a container of the synthetic peptide. Also, the synthetic peptide or C1q fragment may be used to treat an inflammatory response in a mammal by administering to the mammal at the site of inflammation an amount of the C1q fragment or synthetic peptide effective to inhibit the binding of immune complexes by C1q.

Finally, the invention provides a binding material for removing immune complexes or aggregated immunoglobulins from a fluid. The material comprises plural binding peptides, the peptides being characterized in that a plurality of them selectively binds immune complexes and aggregated immunoglobulins in the presence of monomeric immunoglobulin. Preferably, the binding peptides are the C1q fragments of the invention or synthetic peptides comprising the sequence Leu Glu Gln Gly Glu Asn Val Phe Leu Gln Ala Thr [SEQ ID NO 2]
1           5                        10 or a combination of the two. Immune complexes and aggregated immunoglobulins can be removed from fluids containing them by contacting the fluids with the binding material at a temperature and for a time sufficient to bind the immune complexes and aggregated immunoglobulins to the material, and then separating the fluid from the material. The invention also provides a device for removing immune complexes or aggregated immunoglobulins from a fluid comprising the binding material and a means for encasing the material so that the fluid can be contacted with it.

BRIEF DESCRIPTION OF THE DRAWINGS

FIG. 1: Shown are the sequences (from top to bottom) of S. aureus Protein A fragment B, the predicted helical region of C1q, and CBP2 (Peptide (SEQ ID NO 3).

DETAILED DESCRIPTION OF THE PRESENTLY PREFERRED EMBODIMENTS

Figure 2:
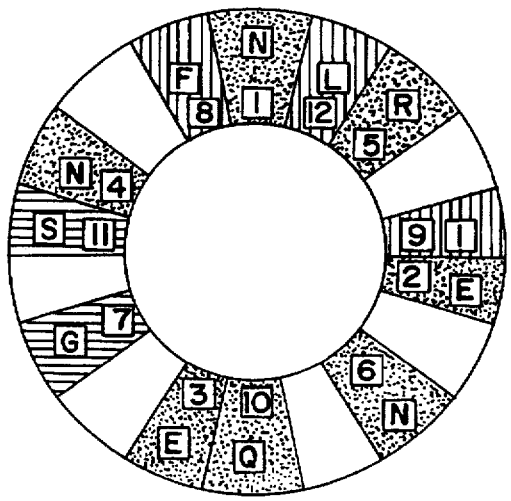
FIG. 2: Helical wheel diagrams for the helical region of Protein A (residues 142–153), predicted helical region of C1q B chain (residues 189–200), and CBP2.
Figure 2:
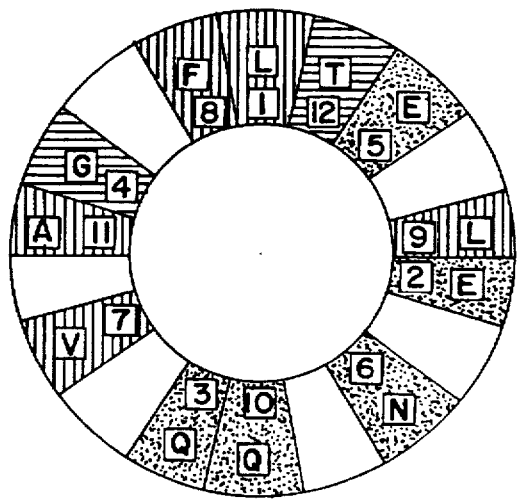
Figure 2:
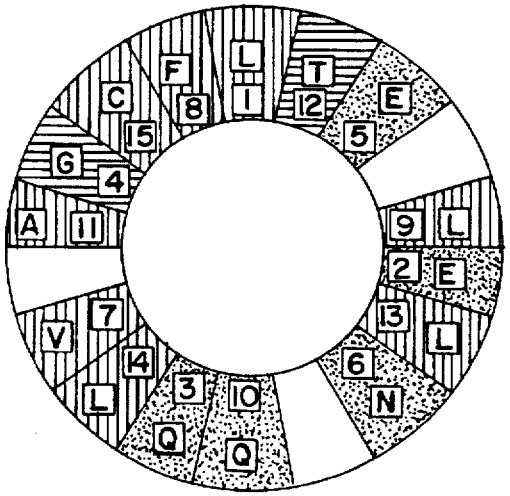

The C1q fragment of the invention may be any fragment of a C1q molecule, a plurality of which selectively binds immune complexes and aggregated immunoglobulins in the presence of monomeric immunoglobulin. The fragment may be a fragment of a C1q molecule of any species, such as human or rabbit. Suitable fragments may be identified as described in Example 1 below. The C1q fragment identified in Example 1 has the sequence Leu Glu Gln Gly Glu Asn Val Phe Leu Gln Ala Thr  [SEQ ID NO 2]
1                   5                       10 and other suitable fragments may be identified by examining the amino acid sequences of C1q molecules for sequences homologous to this C1q fragment.

The invention also provides synthetic peptides comprising the sequence:

Leu Glu Gln Gly Glu Asn Val Phe Leu Gln Ala Thr  [SEQ ID NO 2]
1                   5                       10 or variants thereof capable of binding immunoglobulin. The synthetic peptides are also characterized in that a plurality of them selectively binds immune complexes and aggregated immunoglobulins in the presence of monomeric immunoglobulin.

The most preferred synthetic peptide has the sequence:

Leu Glu Gln Gly Glu Asn Val Phe Leu Gln     [SEQ ID NO 3]
1                   5                  10

Ala Thr Leu Leu Cys
              15

The sequence
Leu Glu Gln Gly Glu Asn Val Phe Leu Gln Ala Thr of SEQ ID NO 3 is that of the C1q fragment identified above (SEQ ID NO 2). The two leucine residues were added to the carboxyl terminus of this fragment as spacing residues to separate the potentially active residues from a future solid phase support (see below). The cysteine residue was added to the carboxyl terminus to allow for coupling of the peptide to solid phases. This preferred synthetic peptide is identified herein as CBP2.

As used herein, a "synthetic peptide" means a peptide which is not a naturally-occurring peptide, although "synthetic peptides" may be altered versions of naturally-occurring peptides. "Synthetic peptides" include peptides synthesized in vitro and peptides synthesized in vivo. In particular, "synthetic peptides" include peptides produced in transformed host cells by recombinant DNA techniques.

As used herein, "variant" means a synthetic peptide having changes (additions, deletions, or substitutions) in the specified amino acid sequence, provided that the "variant" synthetic peptide still has the ability to bind immunoglobulin. "Variants" can have a higher or lower affinity for immunoglobulin than the specified sequence, but all synthetic peptides according to the invention are characterized in that a plurality of them will selectively bind immune complexes and aggregated immunoglobulins in the presence of monomeric immunoglobulin. Preferred "variants" are those in which changes in the specified sequence are made so that the resulting sequence will assume an alpha helical structure when modeled by secondary structure prediction programs.

The C1q fragment or synthetic peptide may be made in a variety of ways. For instance, solid phase synthesis techniques may be used. Suitable techniques are well known in the art, and include those described in Merrifield, in *Chem. Polypeptides*, pp. 335-61 (Katsoyannis and Panayotis eds. 1973); Merrifield, *J. Am. Chem. Soc.*, 85, 2149 (1963); Davis et al., *Biochem. Int'l*, 10, 394–414 (1985); Stewart and Young, *Solid Phase Peptide Synthesis* (1969); U.S. Pat. No. 3,941,763; Finn et al., in *The Proteins*, 3rd ed., vol. 2, pp. 105–253 (1976); and Erickson et al. in *The Proteins*, 3rd ed., vol. 2, pp. 257–527 (1976). Solid phase synthesis is the preferred technique of making individual C1q fragments and synthetic peptides since it is the most cost-effective method of making small peptides.

The C1q fragment and synthetic peptide may also be made in transformed host cells using recombinant DNA techniques. To do so, a recombinant DNA molecule coding for the fragment or peptide is prepared. Methods of preparing such DNA molecules are well known in the art. For instance, sequences coding for the C1q fragment could be excised from C1q genes using suitable restriction enzymes. Alternatively, the DNA molecule could be synthesized using chemical synthesis techniques, such as the phosphoramidite method. Also, a combination of these techniques could be used.

The invention also includes a vector capable of expressing the C1q fragment or synthetic peptide in an appropriate host. The vector comprises the DNA molecule that codes for the C1q fragment or synthetic peptide operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The vector must contain a promoter and a transcription termination signal, both operatively linked to the DNA molecule coding for the C1q fragment or synthetic peptide. The promoter may be any DNA sequence that shows transcriptional activity in the host cell and may be derived from genes encoding homologous or heterologous proteins (preferably homologous and either extracellular or intracellular proteins, such as amylases, glycoamylases, proteases, lipases, cellulases and glycolytic enzymes).

The promoter may be preceded by upstream activator and enhancer sequences. An operator sequence may also be included downstream of the promoter, if desired.

The vector should also have a translation start signal immediately preceding the DNA molecule, if the DNA molecule does not itself begin with such a start signal. There should be no stop signal between the start signal and the end of the DNA molecule coding for the C1q fragment or the synthetic peptide.

Expression control sequences suitable for use in the invention are well known. They include those of the *E.coli* lac system, the *E.coli* trp system, the TAC system and the TRC system; the major operator and promotor regions of bacteriophage lambda; the control region of filamentaceous single-stranded DNA phages; the expression control sequences of other bacteria; promoters derived from genes coding for *Saccharomyces cerevisiae* TPI, ADH, PGK and alpha-factor; promoters derived from genes coding for *Aspergillus oryzae* TAKA amylase and *A. niger* glycoamylase, neutral alpha-amylase and acid stable alpha-amylase; promoters derived from genes coding for *Rhizomucor miehei* aspartic proteinase and lipase; and other sequences known to control the expression of genes of prokaryotic cells, eukaryotic cells, their viruses, or combinations thereof.

The vector must also contain one or more replication systems which allow it to replicate in the host cells. In particular, when the host is a yeast, the vector should contain the yeast 2u replication genes REP1-3 and origin of replication.

The vector should further include one or more restriction enzyme sites for inserting the DNA molecule coding for the C1q fragment or synthetic peptide and other DNA sequences into the vector, and a DNA sequence coding for a selectable or identifiable phenotypic trait which is manifested when the vector is present in the host cell ("a selection marker").

Suitable vectors for use in the invention are well known. They include pUC (such as pUC8 and pUC4K), pBR (such as pBR322 and pBR328), pUR (such as pUR288), phage λ and YEp (such as YEp24) plasmids and derivatives thereof.

In a preferred embodiment, a DNA sequence encoding a signal or signal-leader sequence, or a functional fragment thereof, is included in the vector between the translation start signal and the DNA molecule coding for the C1q fragment or synthetic peptide. A signal or signal-leader sequence is a sequence of amino acids at the amino terminus of a polypeptide or protein which provides for secretion of the protein or polypeptide from the cell in which it is produced. Many such signal and signal-leader sequences are known.

By including a DNA sequence encoding a signal or signal-leader amino acid sequence in the vectors of the invention, the C1q fragment or syntketic peptide encoded by the DNA molecule may be secreted from the cell in which it is produced. Preferably, the signal or signal-leader amino acid sequence is cleaved from the fragment or peptide during its secretion from the cell. If not, the fragment or peptide should preferably be cleaved from the signal or signal-leader amino acid sequence after its isolation.

Signal or signal-leader sequences suitable for use in the invention include *Saccharomyces cerevisiae* alpha factor (see U.S. Pat. No. 4,546,082), *S. cerevisiae* a factor (see U.S. Pat. No. 4,588,684), and signal sequences which are normally part of precursors of proteins or polypeptides such as the precursor of interferon (see U.S. Pat. No. 4,775,622).

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity to it of the C1q fragment or synthetic peptide encoded for by the DNA molecule, rate of transformation, ease of recovery of the C1q fragment or synthetic peptide, expression characteristics, bio-safety and costs. A balance of these factors must be struck with the understanding that not all hosts may be equally effective for the expression of a particular DNA sequence.

Within these general guidelines, useful microbial hosts include bacteria (such as *E. coli* sp.), yeast (such as Saccharomyces sp.) and other fungi, insects, plants, mammalian (including human) cells in culture, or other hosts known in the art.

Next, the transformed host is cultured under conventional fermentation conditions so that the desired C1q fragment or synthetic peptide is expressed. Such fermentation conditions are well known in the art.

Finally, the C1q fragment or synthetic peptide is purified from the culture. These purification methods are also well known in the art.

The C1q fragment or synthetic peptide may be utilized to bind aggregated immunoglobulin or immune complexes. The C1q fragment or the synthetic peptide may be added directly to a fluid containing the aggregated immunoglobulin or immune complexes, or may be attached to a solid phase before being contacted with the fluid containing the aggregated immunoglobulin or immune complexes.

As noted above, a plurality of the C1q fragments or of the synthetic peptides selectively binds to immune complexes or aggregated immunoglobulins in the presence of monomeric immunoglobulin. This makes the C1q fragments and synthetic peptides particularly well-adapted to bind immune complexes and aggregated immunoglobulins in fluids containing monomeric immunoglobulin and for detecting or quantitating immune complexes in such fluids. Fluids which may contain immune complexes or aggregated immunoglobulins, as well as monomeric immunoglobulin, include body fluids (such as blood, plasma and serum) and reagent and pharmaceutical products (such as animal sera, solutions of gamma globulin, isolated blood components, solutions containing monoclonal antibodies, etc.).

Individual C1q fragments and synthetic peptides have a low affinity for immunoglobulins, including those in immune complexes and aggregated immunoglobulins. Accordingly, the plurality of C1q fragments or synthetic peptides must be held in sufficient proximity to each other so that multiple points of attachment to the immune complex or aggregated immunoglobulins can be made and a functional affinity formed (see the discussion of functional affinity in the Background section). This can be accomplished by forming oligomers of the C1q fragments or synthetic peptides (i.e., multiple copies of the C1q fragment or synthetic peptide on the same molecule) or by attaching the C1q fragments or synthetic peptides to a solid phase at an effective density.

On the oligomers, the C1q fragments and synthetic peptides will be spaced an adequate distance apart to permit the formation of multiple points of attachment with immune complexes and aggregated immunoglobulins. As a result, the oligomer will have a higher affinity for immune complexes and aggregated immunoglobulins than for monomeric immunoglobulin (i.e., a functional affinity). If necessary, amino acid spacers can be used between the C1q fragments and synthetic peptides to achieve the proper spacing. The oligomers can be prepared in the same ways as described above for the C1q fragment and synthetic peptide. The oligomers may also be attached to a solid phase as described below.

C1q fragments or synthetic peptides may also be attached to a solid phase at an effective density. An effective density is one that allows the immunoglobulin binding sites of the C1q fragments and synthetic peptides to be spaced apart on the surface of the solid phase in such a manner as to permit multiple point attachment with the immune complexes or aggregated immunoglobulins. At this density, the C1q fragments and synthetic peptides will bind immune complexes and aggregated immunoglobulins in preference to monomeric immunoglobulin because a functional affinity develops. A density which is so low that the spacing of the C1q fragments or synthetic peptides exceeds the distance between binding sites on the immune complexes or aggregated immunoglobulins must be avoided. The density of C1q fragment or synthetic peptide which works best can be determined empirically and will depend on such factors as the surface area of the solid phase material, mode of coupling, the specific nature of the C1q fragment or synthetic peptide used, and the size of the immune complexes or aggregated immunoglobulins.

The C1q fragments, synthetic peptides and oligomers may be attached to any known solid phase material. For the C1q fragments and synthetic peptides, a solid phase which has a relatively non-porous surface is preferably used. Since the C1q fragments and synthetic peptides are small molecules, it is believed that they may become attached to the solid phase in the pores of a porous material. They may, therefore, bind immune complexes or aggregated immunoglobulins less readily since immune complexes and aggregated immunoglobulins are very large molecules which may not be able to enter the pores.

Suitable solid phase materials are well known in the art. Examples include silica, polyacrylamide, polymethylmethacrylate, polycarbonate, poly-acrylonitrile, polypropylene, polystyrene, latex beads and nylon. Commercial sources of suitable solid phase materials include ChromatoChem (Missoula, Mont.), Pharmacia Fine Chemicals (Uppsala, Sweden), and others.

Also, the C1q fragment or synthetic peptide is preferably covalently attached to the solid phase material. Methods and agents for affecting this covalent attachment are well known in the art. Suitable agents include carbodiimide, cyanoborohydride, diimidoesters, periodate, alkylhalides, succinimides, dimethylpimelimidate and dimaleimides [See Blait, A. H., and Ghose, T. L., *J. Immunol. Methods*, 59: 129 (1983); Blair, A. H., and Ghose, T. I., *Cancer Res.*, 41: 2700 (1981); Gauthier, et al., *J. Expr. Med.*, 156: 766–777 (1982)].

The C1q fragment or synthetic peptide is also preferably attached to the solid phase material by means of a spacer arm. The purpose of the spacer arm is to allow the fragment or peptide to be far enough away from the surface of the solid phase so that it can interact with the immune complexes and aggregated immunoglobulins which are very large molecules.

Suitable spacer arms include aliphatic chains which terminate in a functional group such as amino, carboxyl, thiol, hydroxyl, aldehyde, or maleimido, which is active in a coupling reaction. The spacer arm may be located on the solid phase or on the C1q fragment or synthetic peptide or, preferably, there is a spacer arm on both. If the spacer arm is located on the C1q fragment or synthetic peptide, it is preferably a peptide containing less than ten amino acids, preferably two to three amino acids.

The invention also comprises a method of detecting or quantitating immune complexes comprising contacting the immune complexes with the C1q fragment or the synthetic peptide so that the immune complexes bind to the fragment or the peptide. The C1q fragment or synthetic peptide may be added directly to fluids containing the immune complexes or may be attached to a solid phase of the types, and in the ways, described above.

The immune complexes can be detected or quantified using a labeled component that binds to the immune complexes or to the C1q fragment or synthetic peptide. For instance, labeled antibody to immunoglobulin could be used. The labels useful in the invention are those known in the art such as $I^{125}$, biotin, enzymes, fluorophores, bioluminescent labels and chemiluminescent labels. Methods of binding and detecting these labels are standard techniques known to those skilled in the art.

The immune complexes can be detected or quantitated using conventional immunoassay techniques. Such techniques include agglutination, radioimmunoassay, enzyme immunoassays and fluorescence assays. Enzyme immunoassays (EIA) are preferred since they provide a means for sensitive quantitation of levels of immune complexes. The specific concentrations, the temperature and time of incubation, as well as other assay conditions, can be varied in whatever immunoassay is employed depending on such factors as the concentration of the immune complexes or aggregated immunoglobulins in the sample, the nature of the sample and the like. Those skilled in the art will be able to determine operative and optimal assay conditions for each determination while employing routine experimentation.

Since body fluids from mammals normally contain immune complexes, comparison of the levels of immune complexes in a test sample from a mammal will have to be made to the levels found in normals to identify levels of immune complexes indicative of a disease state.

A test kit for detecting or quantitating immune complexes is also part of the invention. The kit is a packaged combination of one or more containers holding reagents useful in performing the immunoassays of the invention.

The kit will comprise a container of the C1q fragment or a container of the synthetic peptide. The C1q fragment or synthetic peptide may be in solution or attached to a solid phase. The solid phases are the types described above, and the C1q fragment or synthetic peptide is attached as described above.

The kit may further comprise a container holding the above-described labeled component that reacts with either the immune complexes or the C1q fragment or synthetic peptide. Finally, the kit may also contain other materials which are known in the art and which may be desirable from a commercial and user standpoint. Such materials include buffers, enzyme substrates, diluents, standards, etc.

The C1q fragment or synthetic peptide can also be used as an anti-inflammatory drug. Inflammation in some diseases, such as rheumatoid arthritis, has been associated with the deposition of immune complexes in tissues and the activation of the complement cascade. It is the binding of C1q to immune complexes deposited in the tissues which intitiates the complement cascade, and the action of the complement components, alone or concurrently with other biologic molecules, ultimately leads to tissue damage.

Accordingly, a C1q fragment or synthetic peptide according to the invention can be administered to a mammal suffering from inflammation mediated by the classical complement pathway to inhibit the binding of immune complexes by C1q and, thereby, prevent tissue damage and further inflammation. The C1q fragments or synthetic peptides are preferably injected at the site of inflammation in the mammal in order to obtain an adequate local concentration of C1q fragments or synthetic peptides. The advantage of such a therapeutic approach is that small peptides are less likely to illicit an immune response which would render the drug inactive.

Finally, the invention provides a binding material for removing immune complexes or aggregated immunoglobulins from a fluid. The material comprises plural binding peptides, the peptides being characterized in that a plurality of them selectively binds immune complexes or aggregatged immunoglobulins in the presence of monomeric immunoglobulin. Preferably, the binding peptides are the C1q fragments of the invention or synthetic peptides comprising the sequence Leu Glu Gln Gly Glu Asn Val Phe Leu Gln Ala Thr     [SEQ ID NO 2]
1       5           10 or combinations of the two.

Individual binding peptides have a low affinity for immunoglobulin. Accordingly, the plurality of binding peptides must be held in sufficient proximity to each other so that multiple points of attachment to the immune complex or aggregated immunoglobulins can be made and a functional affinity is formed. This can be accomplished by forming oligomers of the binding peptides or by attaching the binding peptides to a solid phase at an effective density as described above for the C1q fragments and synthetic peptides. The methods of preparation, and properties, of the resulting oligomers and solid phase materials are as described above for the C1q fragments and synthetic peptides. Also, the oligomers of C1q fragments or synthetic peptides and the solid phase materials having C1q fragments or synthetic peptides attached to them at an effective density that are described above are examples of binding materials according to the invention.

Immune complexes and aggregated immunoglobulins can be removed from fluids containing them by contacting the fluids with the binding material, and then separating the fluid from the binding material. The fluid is simply contacted with the binding material. Such contact can be effected by passing the fluid through a device containing the binding material so that the fluid may contact the binding material. Alternatively, the fluid may be incubated statically with the binding material in the device. The duration of the contact is not bound to critical limits although it should, of course, be sufficient to allow aggregated immunoglobulin or immune complexes to be bound by the binding peptides. The binding material of the invention is especially well-adapted to be used to remove aggregated immunoglobulins or immune complexes from fluids containing monomeric immunoglobulin such as those listed above.

The invention also comprises a device for removing immune complexes or aggregated immunoglobulins from a fluid. The device comprises the binding material and a means for encasing the material so that the fluid can be contacted with it. Binding materials having binding peptides attached to a solid phase are preferred.

The encasing means may be a plastic bag, a column, a test tube, plastic tubing, encasing means like those used on plasmapheresis devices, and other suitable encasing means. The encasing means should be made of a material which is not harmful to the fluid to be placed in the device.

Thus, the device may be a typical plasmapheresis device in which the solid phase is a membranous surface or hollow fibers to which the binding peptides are attached. The device may also be a column packed with beads or any suitable solid phase having the binding peptides attached to it. The device may be a test tube filled with beads to which the binding peptide is attached.

Other devices are also possible. For instance, the binding material may be beads (such as silica beads) to which the binding peptides are attached at a suitable density to selectively remove immune complexes or aggregated immunoglobulins from fluids containing monomeric immunoglobulin. The means for encasing the beads may be a plastic bag of e.g., the type used for transfusions. The fluid containing the immune complexes or aggregated immunoglobulins is mixed with the beads in the bag and incubated for a time, and at a temperature, sufficient to allow the immune complexes or aggregated immunoglobulins to bind to the binding peptides. Then the beads are allowed to settle (or may be centrifuged), and the fluid, from which immune complexes have been removed, is decanted.

For therapeutic uses, a solid phase binding material can be encased online in an extracorporeal device through which whole blood or plasma can be circulated dynamically so that the immune complexes contained therein are bound and removed from the blood or plasma. An alternative would be to statically incubate the whole blood or plasma in a device such as the plastic bag device described above. In either case, fluids can be returned to the body after the incubation or passage is complete, negating the need for blood replacement therapy.

A device intended for therapeutic use may also include appropriate tubing for connecting it to a patient and a pump to aid the passage of the fluid through the device and back into the patient and to prevent air from entering the system. The device must be sterilized for therapeutic use, and sterilization may be accomplished in conventional ways such as purging with ethylene oxide or by irradiating the device.

EXAMPLES

Unless otherwise indicated, the chemicals used in the following Examples were obtained from Sigma Chemical Co., St. Louis, Mo.

Example 1

Peptide Synthesis

A. Peptide Design and Structure

X-ray crystal structural data for Protein A Fragment B indicated that two coplanar α-helical segments with the proper contact residues (see Background) could bind immunoglobulin Fc with a high affinity. Deisenhofer et al., *Hoppe-Seyler's Z. Physiol. Chem. Bd.*, 359, S. 975–85 (1978); Burton, *Molec. Immunol.*, 25, 1175–81 (1988); Langone, *Adv. Immunol.*, 32, 157–252 (1982). As discussed above, C1q also binds IgG Fc. Thus, the question was posed whether C1q bound IgG Fc using structures similar to those found in Protein A Fragment B. Unfortunately, structural information regarding the C1q molecule was limited, and information concerning the C1q binding site for immunoglobulin was nonexistent.

However, the amino acid sequences of the entire A and B chains and a partial sequence for the C chain of C1q were available. Reid, *Biochemical J.*, 179, 367–71 (1978); Reid, et al., *Biochemical J.*, 203, 559–69 (1982). These sequences were analyzed by the secondary structure prediction programs of Garnier et al., *J. Molec. Biol.*, 120, 97–120 (1978) and Chou and Fasman, *Adv. Enzym.*, 47, 45–146 (1978). Of the predicted alpha helical regions, one helical region in the C1q B chain globular head region spanned 12 residues, suggesting a high probability that the helix prediction was accurate.

The predicted helical segment of C1q B chain (residues 189–200) was then compared to one Protein A Fragment B helix (residues 142–153), and homology was observed (see FIG. 1). Four amino acids were exact matches, while three additional residues showed conservative substitutions. Out of three possible contact residues on the Protein A helix, C1q possessed two similar residues. Further analysis of the two sequences was achieved through the use of helical wheel diagrams (FIG. 2). These diagrams showed that the pattern of hydrophobic and hydrophilic residues observed for the Protein A helix known to contact immunoglobulin was similar to that of the predicted C1q helix.

Therefore, the 12-residue sequence of C1q having the predicted helical structure was synthesized. Two Leu residues were added to the carboxyl-terminus as spacing residues to separate the potentially active residues from a future solid phase matrix. A Cys residue was also added to the carboxyl-terminus to allow for coupling to solid phases using certain coupling procedures. The final amino acid sequence, designated CBP2, is presented in FIG. 1.

B. Synthesis

The CBP2 sequence was submitted to Biosearch Inc. (San Rapheal, Calif.) for custom peptide synthesis using the standard Merrifield solid phase synthesis approach. Merrifield, in *Chem. Polypeptides*, pp. 335–61 (Katsoyannis and Panayotis eds., Plenum, New York, N.Y. 1973). Approximately 250 mg of the peptide in lyophilized form were obtained.

Biosearch's quality control information was based on amino acid analysis and analytical reverse phase HPLC. The chromatograph provided by Biosearch showed that the initial purity of the peptide was approximately 40–50%. Biosearch did not provide the results of the amino acid analysis, but they stated that the composition of the peptide had to be within ±20% of the calculated values for each amino acid of the peptide in order to pass their quality control. Therefore, the CBP2 peptide should have had the correct amino acid sequence.

C. Purification

In addition to the purification performed by Biosearch, the peptide was further purified by gel filtration chromatography. The lyophilized CBP2 was not soluble in aqueous solvents and required 50% (v/v) N,N-dimethylformamide (DMF) (J. T. Baker Chemicals, Phillipsburg, N.J.) to completely dissolve. Due to the high hydrophobic character of the solvent, Sephadex G25 (Pharmacia, Piscataway, N.J.) was used for the chromatography. A column of dimensions 0.7×40 cm was poured and equilibrated with 1% (v/v) DMF in distilled water (dH$_2$O). A 2 mg/ml sample of CBP2 was prepared in 50% (v/v) DMF, and 1 ml of the sample was loaded on the column and eluted with 1% DMF at a flow rate of 1 ml/15 min. One ml fractions were collected.

The column fractions were assayed for peptide by the Bicinchoninic Acid (BCA) protein assay (Pierce Chemical Co., Rockford, Ill.) according to the manufacturer's instructions. Briefly, duplicate 30 µl aliquots from each fraction were placed in the wells of a microtiter plate, followed by the addition of 300 µl of BCA protein reagent. In addition to the column fractions, samples ranging from 1 mg/ml to 0.1 µg/ml Val-Gly-Gly peptide (Sigma Chemical Co., St. Louis, Mo.) were also added to the microtiter plate to prepare a standard curve. The plate was incubated at 37° C. for 1 hour, and the resultant colored product measured using a TiterTek Multiskan plate reader (Flow Laboratories, McLean, Va.) at 560 nm. The absorbances were then plotted against fraction number to generate the chromatogram.

A 1% (v/v) DMF sample was also tested in the BCA assay as a control. DMF was shown by these experiments not to interfere with the detection of the peptides in the column fractions.

Figure 3:
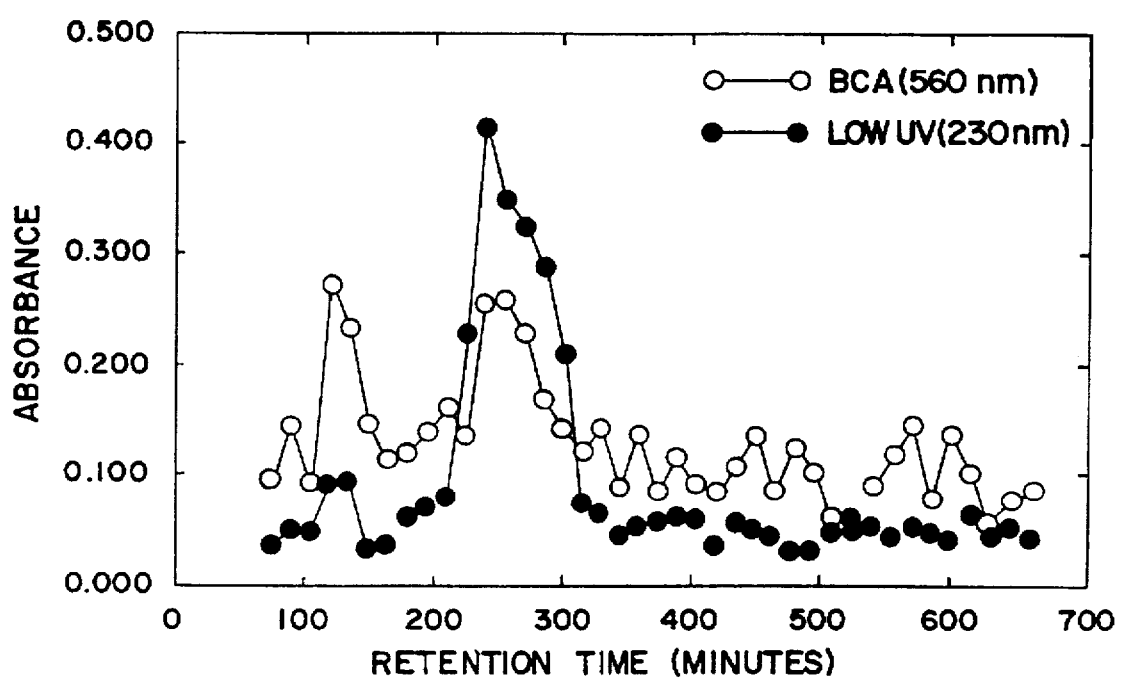
FIG. 3: Shows the elution profile of CBP2 on a Sephadex G25 column.

A 1.2 fold increase in peptide purity with a 41% yield of peptide was obtained. A representative chromatograph for CBP2 is shown in FIG. 3. The profile showed a symmetrical major peak at 250 minutes and several minor peaks representing contaminants. It should also be noted that purified CBP2 was readily soluble in 1% (V/V) DMF, indicating that it may be the impurities in lyophilized CBP2 that could only be dissolved in 50% DMF.

In addition to the standard BCA assay for peptides, the absorbance profile for CBP2 migrating in the Sephadex G25 column was measured at 230 nm. The absorbance profile shown in FIG. 3 confirms the results of the BCA assay in that the CBP2 peak had a retention time of 250 minutes. It is important to note that the UV absorbance profile at 230 nm is most sensitive to amide bonds. Since the CBP2 peak was the major source of absorbing material, the remaining impurities may not contain amide bonds and, therefore, may not be peptides.

The CBP2 retention time in the Sephadex G25 column suggested a larger molecular weight than the calculated molecular weight based on the amino acid sequence of the peptide. Therefore, under the same conditions, samples of glucagon, LHRH, and a mixture of glucagon and LHRH were loaded and eluted from the Sephadex G25 column. Glucagon (3550 daltons) had a retention time of 247 minutes and LHRH (1182.33 daltons) had a retention time of 277.4 minutes. CBP2 (1556.98 daltons) had a retention time similar to glucagon, suggesting that CBP2 migrated through the Sephadex G25 column as an aggregate of at least two peptides. Concentration dependent aggregation of amphipathic peptides has been documented. DeGrado et al., *J. Am. Chem. Soc.*, 103, 679–81 (1981); Taylor et al., *Mol. Pharmacol.*, 22, 657–66 (1982); Moe and Kaiser, *Biochem.*, 24, 1971–76 (1985).

Analytical C$_{18}$ reverse phase HPLC was used in order to assess the purity of the CBP2 isolated from the Sephadex G25 column. The conditions used for the chromatography were the same as those used by Biosearch. Briefly, 500 µg/ml of CBP2 in 1% (v/v) DMF in dH$_2$O and 4 mg/ml dithiothreitol (the peptide was incubated over night with the DTT in order to reduce any disulfide bonds that may have formed) were passed over a Vydac (Hesperia, Calif.) C$_{18}$ analytical column (product #218TP54) with dimensions 4.6 mm×25 cm and using the following buffers and conditions. Buffer A: 0.05% (v/v) trifluoroacetic acid (TFA) in dH$_2$O. Buffer B: 0.05% (v/v) TFA in acetonitrile. Column conditions: A 100 µl sample was injected, and 5% buffer B was maintained for 3 min at 1.7 ml/min followed with a gradient of 5–100% buffer B over the next 20 min. The peptide was detected with a Beckman (Palo Alto, Calif.) UV variable wavelength detector at 230 nm.

Figure 4A:
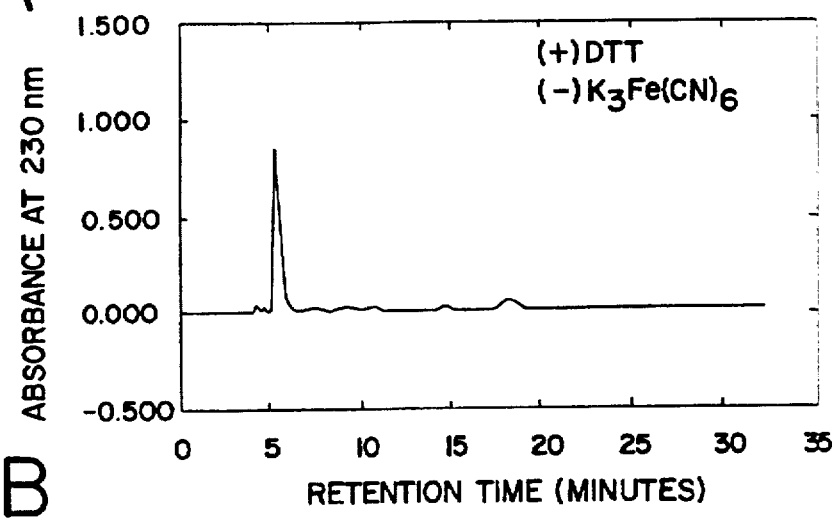
FIG. 4A: Reverse phase High Performance Liquid Chromatography (HPLC) chromatograph of CBP2 under reducing conditions.

It is important to note that CBP2 was treated with DTT overnight before the analysis in order to disrupt any disulfide bonds that may have formed. FIG. 4A shows a representative chromatograph of the reduced isolated CBP2. CBP2 comprised 80% of the absorbing material, indicating that the Sephadex G25 isolated CBP2 was relatively pure. With exception of the peaks at 4.4 minutes, the remaining peaks were retained in the column significantly longer than CBP2, suggesting that the impurities were of smaller molecular weight and/or were much more hydrophobic than CBP2.

Figure 4B:
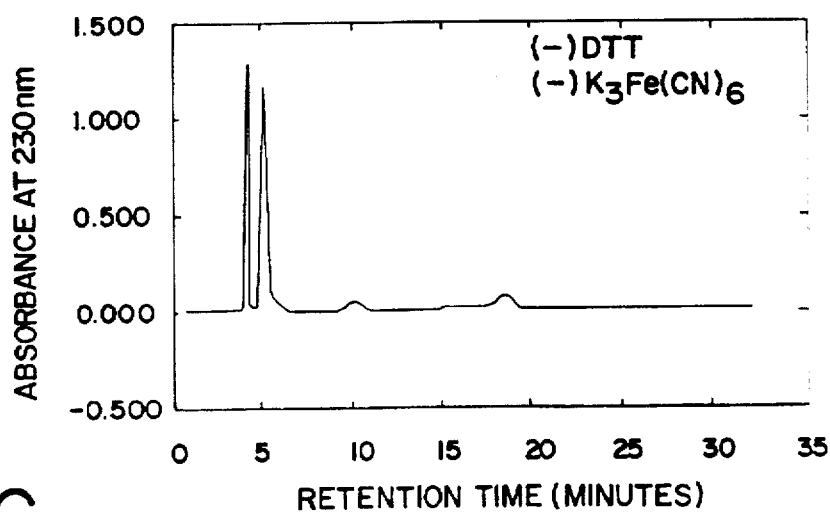
FIG. 4B: Reverse phase HPLC chromatograph of CBP2 under nonreducing conditions.
Figure 4C:
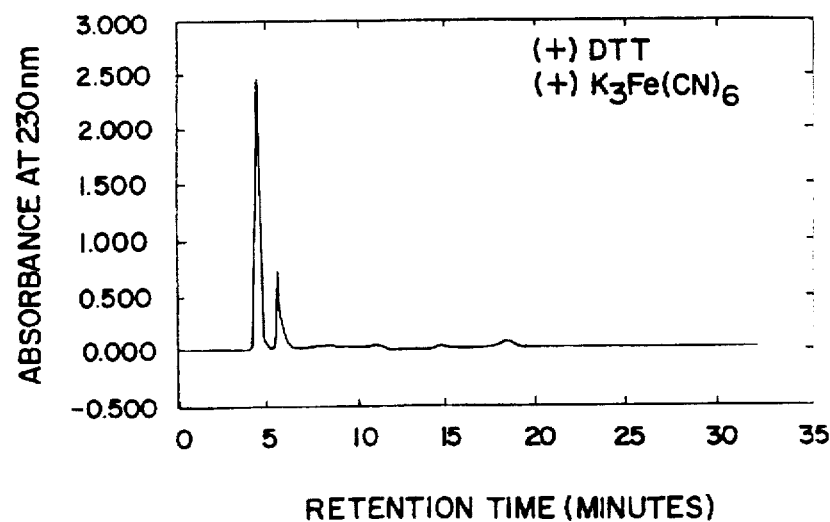
FIG. 4C: Reverse phase HPLC chromatograph of CBP2 in the presence of an oxidizing agent to favor the formation of disulfide linked CBP2 peptides.

Since CBP2 did contain free cysteine residues, it was necessary to determine the CBP2 profile in the absence of DTT to assess the extent of disulfide formation. In addition, K$_3$Fe(CN)$_6$, which would favor the formation of disulfides, was added to the reduced CBP2 solution. This process was necessary to determine the retention time of the disulfide aggregated CBP2. FIG. 4B shows the CBP2 profile without the reduction of disulfides. A strong absorbance peak at 4.4 minutes possessing 28% of the total absorbance was the only significant difference between reduced and nonreduced CBP2 (compare FIGS. 4A and 4B). The addition of $K_3Fe(CN)_6$ to the reduced CBP2 solution and the subsequent analysis showed that the peak at 4.4 minutes in FIG. 4B was due to disulfide aggregated CBP2. In FIG. 4C, the addition of the oxidizing reagent caused a decrease in the reduced CBP2 peak with an accompanying increase in the 4.4 minute peak which represented 68.7% of the total area. Therefore, the 4.4 minute peak was the disulfide aggregated CBP2.

It is important to note that in all three chromatographs in FIG. 4, CBP2 comprises at least 80% of the total area, with the combination of the reduced and nonreduced CBP2 peaks representing approximately 90% of the total area. Based on the results of the three chromatographs, it was concluded that the purity of CBP2 was 80–90%.

D. CD Spectroscopic Analysis Of CBP2

Circular dichroism (CD) spectroscopy was performed on an Aviv 60DS spectropolarimeter. The sample consisted of 200 µl of 200 µg/ml CBP2 dissolved in 10 mM sodium phosphate buffer, pH 7.0, at room temperature. A 1 mm path length was used.

Under these conditions, CBP2 exhibited a CD spectrum characteristic of a random coil peptide. The lack of structure was expected for small peptides such as CBP2.

Example 2

Inhibition Studies

A. Titration of Rabbit Immunoglobulin Bound by Solid Phase Protein A

Protein A (recombinant Protein A from Repligen, Cambridge, Mass.) diluted to 1 µg/ml in coating buffer (0.1M $NaHCO_3$, pH 9.0) was incubated in the wells of a microtiter plate (100 µl per well) for 2 hours at 37° C. Uncoated surfaces of the wells were blocked by adding 340 µl PBSC (9 mM $Na_2HPO_4$, 1 mM $NaH_2PO_4$, pH 7.2, 154 mM NaCl, 1 mg/ml casein or ovalbumin, and 0.01% thimerosal), incubating the plate 1 hour at 37° C., and then washing the wells 3 times with PBSCT (PBSC plus 0.1% Tween 20). Dilutions of rabbit immunoglobulin labeled with horseradish peroxidase (Ig-HRP) (Zymed Laboratories, Inc., South San Francisco, Calif.) in PBS (9 mM $Na_2HPO_4$, 1 mM $NaH_2PO_4$, pH 7.2, 154 mM NaCl) were incubated in the wells (100 µl per well) for 2 hours at 37° C. followed by washing 3 times with PBS. OPD substrate buffer (0.8 mg/ml o-phenylenediamine, 0.1M $Na_2HPO_4$, 0.05M sodium citrate, pH 5.5, plus 0.15% (v/v) $H_2O_2$) was then added to the wells (100 µl/well), and the resultant colored product was measured with a Titertek Multiskan plate reader using a 414 nm filter.

CBP2 Inhibition of Solid Phase Adsorbed Protein A.

It had previously been reported that C1q and Protein A compete exclusively for IgG (Burton, *Molec. Immunol.*, 22, 161–206 (1985); Stalinhelm et al., *Immunochem.*, 10, 501–507 (1973); Langone et al., *J. Immunol.*, 121, 327–38 (1978); Lancet et al., *Biochem. Biophys. Res. Commun.*, 85, 608–614 (1978)). Accordingly, CBP2 was tested for inhibition of the binding of Ig-HRP by Protein A.

The wells of a microtiter plate were coated with Protein A as described above in Part A. Ig-HRP diluted 1:5000 in PBS (the dilution determined by the protein A titration experiment of Part A; original Ig-HRP concentration of 3.3 mg/ml) was preincubated with various concentrations of CBP2 for 1 hour at 37° C. before 100 µl of the incubation mixture were added to each well of the microtiter plate. The CBP2/Ig-HRP mixture was incubated with the solid phase adsorbed Protein A for 2 hours at 37° C. and then washed 3 times with PBS. OPD substrate buffer was then added (100 µl/well), and the resulting colored product was measured at 414 nm in a Titertek Multiskan plate reader. Absorbance readings were made when the control wells with no inhibitor had an absorbance of 1.0 or greater.

Figure 5:
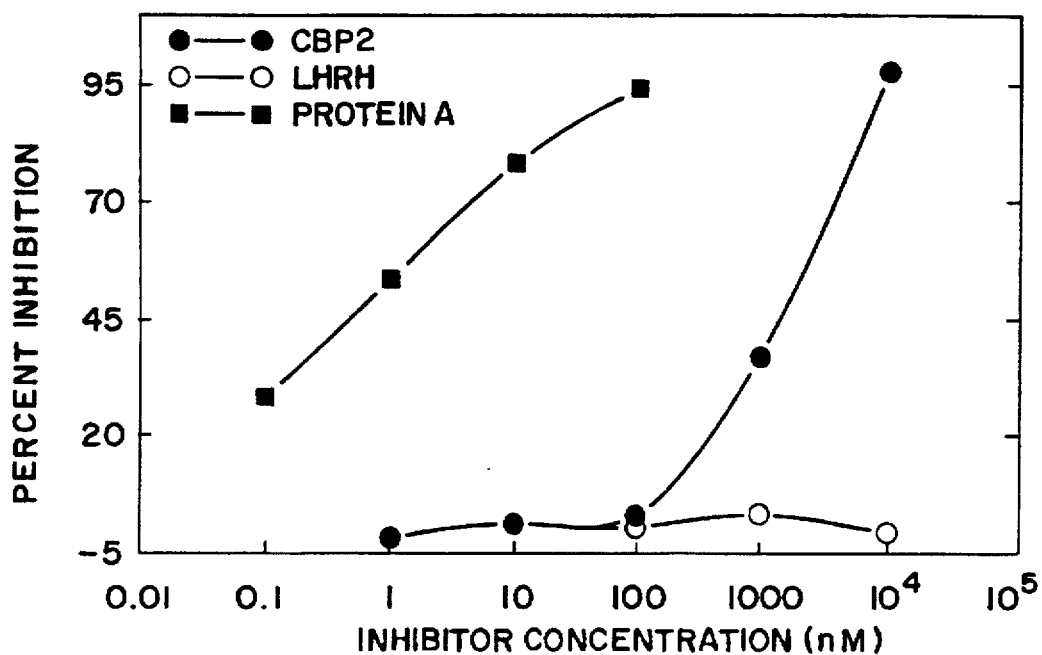
FIG. 5: Shows the inhibition of the binding of immunoglobulin labeled with horseradish peroxidase (Ig-HRP) to solid phase Protein A by CBP2, Protein A, or lutenizing hormone releasing hormone (LHRH).

The results, which are shown in FIG. 5, show that CBP2 was able to inhibit Protein A binding of Ig-HRP by nearly 100%. The concentration at 50% inhibition was approximately 1 µM which is a 1000-fold greater concentration than the 1 nM 50% inhibition concentration for solution phase Protein A (see FIG. 5). Since the 50% inhibition concentration for Protein A is comparable to its dissociation constant, the 50% inhibition concentrations were considered a good measure of the binding affinity of the inhibitor.

C. Titration of Ig-HRP Bound by Solid Phase C1q.

C1q (gift of Dr. Lawrence Potempa, Immtech International Inc., Evanston, Ill.) diluted to 10 µg/ml in coating buffer was placed in the wells of a microtiter plate (100 µl/well) and incubated for 2 hours at 25° C. The uncoated surfaces of the wells were blocked by adding 340 µl PBSC and incubating the plate for 1 hour at 25° C., followed by washing 3 times with PBSC. Dilutions of Ig-HRP in C1q buffer (50 mM Tris, pH 7.2, 27 mM NaCl, 1 mM $CaCl_2$, 0.01% (wt/v) Thimerosal) were incubated in the wells (100 µl/well) for 1 hour at 25° C. followed by washing 3 times with C1q buffer. OPD substrate buffer was then added (100 µl/well), and the colored product was measured at 414 nm in a Titertek Multiskan plate reader.

D. CBP2 Inhibition of Solid Phase C1q.

C1q was coated onto the surface of the wells of a microtiter plate as described in Part C. Ig-HRP diluted 1:100 (the dilution determined from the C1q titration experiment described above in Part C) in C1q buffer was preincubated with various concentrations of CBP2 for 1 hour at 25° C. The Ig-HRP/CBP2 mixture was then added to the microtiter plate (100 µl/well), and the plate was incubated for 1 hour at 25° C., followed by 3 washes with C1q buffer. OPD substrate buffer (100 µl/well) was then added and the colored product measured at 414 nm in a Titertek Mutiskan plate reader.

Figure 6:
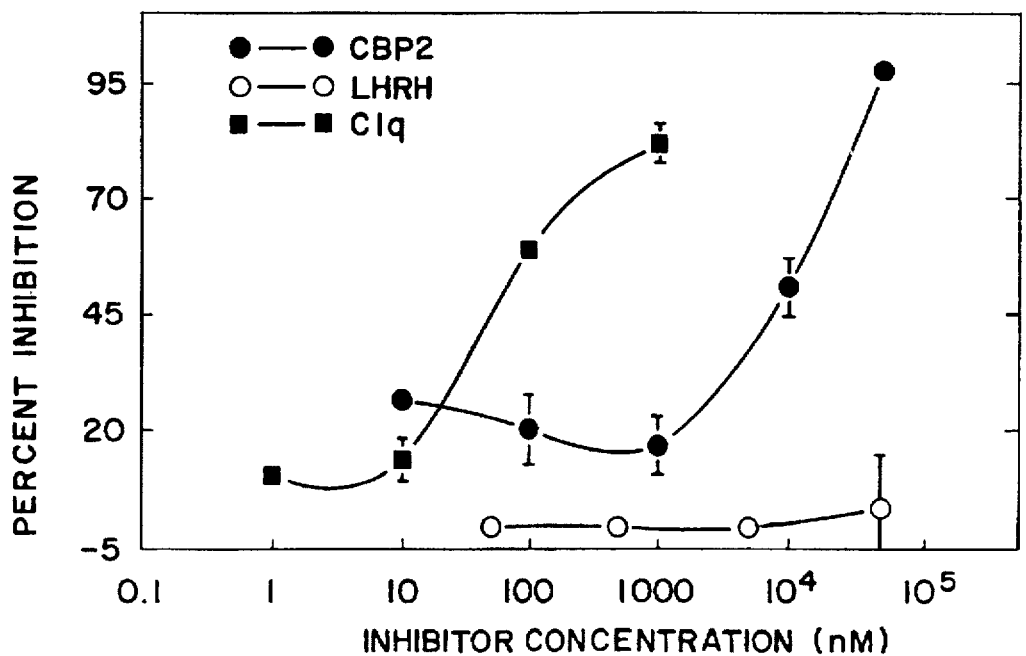
FIG. 6: Shows the inhibition of the binding of rabbit Ig-HRP to solid phase C1q by CBP2, C1q, or LHRH.

The resulting inhibition curve is presented in FIG. 6. The 50% inhibition concentration was approximately 10 µM, which was an order of magnitude higher than the 50% inhibition concentration for CBP2 inhibiting Protein A. The 50% inhibition concentration for liquid phase C1q inhibiting solid phase C1q was approximately 10 nM or 1000 fold less than the CBP2 concentration (see FIG. 6).

E. Control Experiments For CBP2 Inhibition Of Protein A And C1q

In order to conclude that CBP2 was binding immunoglobulin and not causing an inhibition in the assay system through a nonspecific interaction, a series of control experiments were performed.

1. The effects of CBP2 on the HRP enzyme were investigated. Ig-HRP at a 1:100 dilution in PBS or C1q buffer was incubated with 50 µM CBP2 or an equal amount of 1%(v/v) DMF for 3 hours at 37° C. Aliquots of 100 µl were placed in the wells of a microtiter plate and an equal volume of OPD substrate buffer was added, and the colored product was measured at 414 nm. Both the CBP2 and Ig-HRP were at the highest concentrations tested in the inhibition assay. The sample which contained both peptide and Ig-HRP did not differ significantly from the control sample containing the Ig-HRP alone. Therefore CBP2 did not inhibit the HRP enzyme.

2. Protein A at 1 µg/ml or C1q at 10 µg/ml diluted in coating buffer was incubated in the wells of a microtiter plate (100 μl/well) for 2 hours at 37° C. or 25° C., respectively. The wells were blocked in the same fashion as described above for each assay. Various concentrations of CBP2 diluted in PBS or C1q buffer were incubated in the wells (100 μl/well) for 2 hours at 37° C. or 1 hour at 25° C., respectively, followed by washing the wells 3 times with either PBS or C1q buffer. Ig-HRP was then added at the appropriate dilution in either PBS or C1q buffer and incubated under the appropriate conditions, followed by washing 3 times with PBS or C1q buffer. OPD substrate buffer was then added (100 μl/well), and the colored product was measured at 414 nm as described above.

3. Excess protein (1 mg/ml casein) was added to the buffers used to dilute the Ig-HRP/CBP mixture.

Controls 2 and 3 tested for nonspecific protein-protein or protein-peptide interactions. If there were such interactions, then there would be a loss of CBP2's inhibitory activity in test 3, and no such loss was observed. In test 2, any loss in CBP2's inhibitory activity would indicate that CBP2 was blocking the solid phase Protein A or C1q binding sites and not interacting with Ig-HRP. No loss of inhibitory activity was detected.

4. Equal molar concentrations of luteinizing hormone releasing hormone (LHRH) (Beckman Instruments, Palo Alto, Calif.) or various concentrations of Protein A were substituted for CBP2 in the inhibition assay described in Part B. In the case of the C1q inhibition experiments, LHRH and C1q were substituted for CBP2 as a negative and a positive control, respectively. The use of LHRH also tested whether the inhibition of Protein A or C1q by CBP2 was due to CBP2 specifically, or simply due to nonspecific effects attributable to a small peptide. The results are shown in FIGS. 5 and 6. As indicated in these figures, LHRH demonstrated no Protein A or C1q inhibitory activity over the same concentration range examined for CBP2, and both Protein A and C1q were inhibitory, as expected.

5. Concentrations of Ig-HRP required for the C1q assays were 50 fold higher than the concentration used for Protein A assays. The reason for the higher concentration is that only a small fraction of Ig-HRP existed as complexes that could be bound by C1q. This was demonstrated by fractionating the Ig-HRP as follows. A 40 μl sample of Ig-HRP was loaded onto a TSK SW 4000 sizing HPLC column (Beckman/Altex TSK 4000 SW, 7.5 mm×30 cm). Only the high molecular mass eluted fractions exhibited any C1q binding activity as determined by a C1q binding assay performed as described above. The results of this assay indicated that the C1q binding material was a fraction having molecular weight of approximately 1,000 kdal, indicating a complex of immunoglobulins and HRP enzymes, and not a monomeric immunoglobulin plus HRP enzyme.

6. With respect to C1q, nonspecific ionic interactions could not be excluded since the C1q buffer was half-physiological ionic strength. The ionic strength of the C1q buffer could not be changed since C1q binding of immunoglobulins is partially mediated by ionic interactions. However, based on the Protein A inhibitory activity of CBP2 in physiological ionic strengths, it was a reasonable assumption that CBP2 inhibition was not primarily the result of nonspecific ionic interactions.

7. Proteins when adsorbed to the polystyrene wells of a microtiter plate may partially lose their native conformation. Therefore, CBP2 was also screened for any interactions with solution phase Protein A. Protein A was incubated in the wells of a microtiter plate (100 μl/well) for 2 hours at 37° C. at 1 μg/ml in coating buffer, and the wells blocked as described above. Protein A at a constant concentration (corresponding to either 100 times the 50% inhibition concentration, the 50% inhibition concentration, or 10 fold less than the 50% inhibition concentration) was preincubated with CBP2 and Ig-HRP in PBS for 1 hour at 37° C. The Protein A/CBP2/Ig-HRP mixture was then incubated in the wells of the microtiter plate (100 μl/well) for 2 hours at 37° C. and washed 3 times with PBS. OPD substrate buffer was then added (100 μl/well), and the resultant colored product was measured at 414 nm as before.

At Protein A concentrations at or above the 50% inhibition concentration, there was a linear, additive response, indicating no interaction between CBP2 and Protein A. At Protein A concentrations below the 50% inhibition concentration, the curve is analogous to the CBP2 inhibition curve in the absence of solution phase Protein A. This also suggests that CBP2 and Protein A are not interacting.

8. Since the CBP2 peptide has a free cysteine residue, the effects of DTT on the inhibition assay were examined. DTT was added to the buffer containing CBP2 (final DTT concentration 4 mg/ml), and the CBP2 was incubated with the DTT for 2 hours at 37° C. to ensure that the cysteine residues of CBP2 were reduced. Then the inhibition assay using solid phase Protein A was performed as described above.

The addition of DTT to the CBP2 solution had no effect on the inhibitory activity of CBP2. These data indicate that CBP2 does not inhibit by forming disulfide interaction with Protein A or Ig-HRP and that disulfide-mediated CBP2 aggregates did not have a significant influence on CBP2's ability to inhibit the binding of Ig-HRP to Protein A.

F. Conclusions

Based on the inhibition data in conjunction with the above controls, it can be concluded that CBP2 inhibits C1q and Protein A binding of Ig-HRP through a binding interaction with solution phase Ig-HRP. The results indicate that CBP2 binds immunoglobulin in a specific manner.

Example 3

HiPAC™ LTQ Column

A HiPAC™ LTQ (ChromatoChem, Missoula, Mont.) activated aldehyde column of dimensions 7.4 mm×1.9 cm was equilibrated with 6 ml of immobilization buffer (0.1M sodium citrate, pH 5.5). This column is composed of silica beads to which a long carbon chain spacer arm is attached. A ligand coupling solution containing 500 μg CBP2 and 20 mg/ml sodium cyanoborohydride in immobilization buffer was prepared. This was continuously circulated through the column for 5 min at 25° C. at a flow rate of 1–2 ml/min. The coupling solution was then eluted from the column and collected. The column was subsequently washed with 6 ml immobilization buffer which was also collected. The column was then washed with 6 ml of 2% (v/v) acetic acid and equilibrated with 6 ml C1q buffer.

The coupling procedure linked CBP2 to the solid phase support through the N-terminal amino group, leaving the C-terminal cysteine's sulfhydryl available as a marker. The Ellman's reagent assay (Ellman, Arch. Biochem. Biophys., 82, 70–77 (1959)) was, therefore, used to measure the amount of CBP2 bound to the column since Ellman's reagent (5,5-dithio-bis-(2-nitrobenzoic acid)) reacts with free sulfhydryl groups.

To perform the Ellman's reagent assay, the column was first washed with a 4 mg/ml solution of DTT in order remove any peptides linked to the solid phase by disulfide bonds. Then the column was washed with C1q buffer until the eluate showed no reactivity with Ellman's reagent. The column was then equilibrated with 6 ml of 0.1N $Na_2HPO_4$, pH 8.0. Next, 1 ml of a solution of 400 µg/ml Ellman's reagent in 0.1N $Na_2HPO_4$, pH 8.0, was continuously passed over the column for 15 min. The Ellman's reagent solution was eluted from the column, collected, and the column washed with 6 ml of 0.1N $Na_2HPO_4$, pH 8.0. One ml of a 4 mg/ml solution of DTT was passed over the column, and the eluate was collected. The column was then washed with 6 ml C1q buffer and the eluates collected. The resulting colored products were measured at 412 nm.

The moles of CBP2 coupled to the column were proportional to the moles of Ellman's reagent reacting with the column (i.e., the amount of Ellman's reagent eluted with the DTT) which was calculated using a molar extinction coefficient of $1.36 \times 10^4$/cm·M for the free thionitrobenzoic acid. The assay of the column indicated that 84% of the CBP2 added to the column was coupled to the solid phase, or approximately 420 µg CBP2.

It should be noted that attempts to measure CBP2 in eluted fractions using various techniques (BCA assay, UV spectroscopy, 2,4,6-trinitrobenzene sulfonic acid and the Ellman's reagent assay) were unsuccessful because the cyanohydride reagent interferred with those assays.

Two control columns were prepared along with the CBP2 column. LHRH was coupled to the matrix in the same fashion as CBP2 and at the same concentration as CBP2 as determined by UV spectroscopy. A similar percentage (78%) of LHRH was coupled to the column by reductive amination as with CBP2 (84%). Another column was treated in the same fashion as the CBP2 and LHRH columns, but no peptide or protein was coupled ("No peptide" column), thus allowing the study of nonspecific binding effects in the following experiments.

Example 4

PAP Binding to the HiPAC™ LTQ-CBP2 Column

A CBP2 column prepared as described in Example 3 was equilibrated with 3 ml C1q buffer. Immune complexes composed of rabbit anti-horseradish peroxidase and horseradish peroxidase (PAP) (purchased from Organon Teknika/Cappel, West Chester, Pa.) at a concentration of 20 µg/ml in C1q buffer (a total volume of 1 ml) were loaded onto the column and incubated for 15 min at 25° C. with continuous circulation through the column. Unbound PAP complexes were eluted with 12 ml C1q buffer (at a flow rate of 0.33 ml/min, collecting 1 ml fractions) followed by 3 ml of 2% (v/v) acetic acid to elute bound PAP.

A. Peroxidase Assays

The column fractions were assayed for peroxidase activity by placing duplicate 20 µl aliquots into the wells of a microtiter plate and adding 100 µl of OPD substrate buffer. The absorbances were measured at 414 nm in a Titertek Multiskan plate reader. The absorbances were then plotted against fraction number to generate the chromatograph. In addition to the samples, a standard curve was prepared, and a linear regression analysis was performed. From the standard curve the concentration of PAP in each fraction was calculated.

Figure 7:
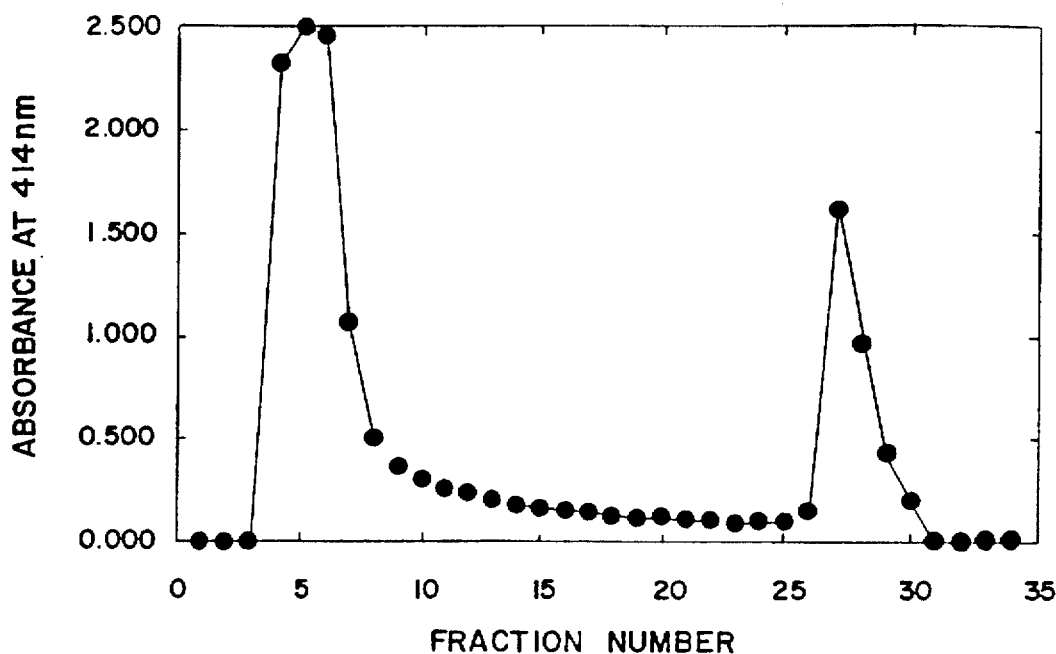
FIG. 7: The elution profile of horseradish peroxidase/anti-horseradish peroxidase immune complexes (PAP) passed over the HiPAC™ LTQ-CBP2 column.

The resulting profile is presented in FIG. 7. The elution profile shows two major peaks. The first peak was material that did not bind to the column and which was readily eluted with C1q buffer. This material appeared to make up the larger fraction of the PAP loaded on the column. In fact, using the standard curve and linear regression analysis, the flow-through peak was calculated to contain approximated 90–95% of the total PAP. The second peak was the material bound by the column and eluted with the acetic acid. The bound material was only 5–10% of the total PAP loaded on the column.

Although the efficiency of the column appeared to be low, the column did bind immune complexes. Therefore, it was determined whether the column bound immune complexes specifically and in a CBP2-dependent manner.

One ml containing PAP complexes at a concentration of 20 µg/ml and monomeric rabbit IgG at a concentration of 80 µg/ml in C1q buffer was loaded on a CBP2 column prepared as described in Example 3, that had been equilibrated with 3 ml of C1q buffer. The PAP/IgG mixture was circulated through the column continuously for 15 min and then eluted with 12 ml C1q buffer at a flow rate of 0.33 ml/min. Material bound to the column was eluted with 3 ml of 2% (v/v) acetic acid followed by 6 ml of C1q buffer. (The flow rates and fractions were the same as for PAP alone.) The fractions were assayed for the presence of peroxidase activity in the same fashion as described above and the concentration of PAP was calculated from the standard curve.

Figure 8:
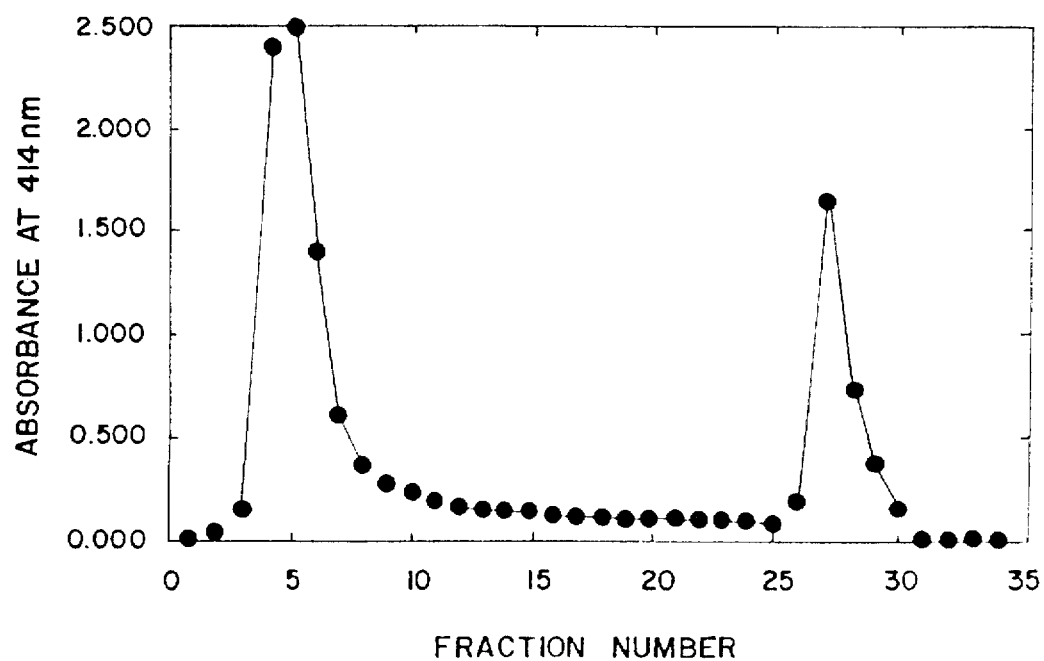
FIG. 8: The elution profile of a mixture of PAP plus monomeric rabbit IgG.

Once again two peaks were observed (FIG. 8). The first peak represented the flow-through, and contained 95% of the total PAP loaded on the column. The amount of material bound to the column in the second peak also remained unchanged at approximately 5%. Since the elution profiles of PAP, both with and without monomeric IgG, were not different with respect to the quantities of material in each peak and the retention times of the peaks, it appeared that the column specifically bound immune complexes.

B. Enzyme Immunoassay For IgG

PAP complexes were loaded onto a CBP2 column and eluted from it as described in Part A. Also, monomeric IgG at a concentration of 80 µg/ml in 1 ml of C1q buffer was loaded onto a CBP2 column and eluted from it in the same manner.

The fractions were then assayed for immunoglobulin by enzyme immunoassay as follows. Duplicate 50 µl aliquots of each fraction were placed in the wells of a microtiter plate. Fifty µl of coating buffer were then added, and the plate was incubated at 37° C. for 2 hours. The uncoated surfaces of the wells were then blocked by adding 340 µl of PBSC, followed by incubation of the plate for 1 hour at 37° C. The wells were washed 3 times with PBSCT, and a 1:2000 dilution of goat anti-rabbit IgG that was labeled with biotin (anti-rabbit IgG) (Vector Laboratories, Inc., Burlingame, Calif.) was added (100 µl/well). The anti-rabbit IgG was incubated in the wells for 2 hours at 25° C., and the wells were washed 3 times with PBSCT. Next, a 1:2000 dilution of streptavidin-β-galactosidase (BRL-Life Technologies, Gaithersberg, Md.) in PBSCT was added to the wells (100µl/well), the plates were incubated for 2 hours at 25° C. and washed 3 times with PBSCT. Fluorogenic substrate in buffer (5 mg/ml of 4-methylumbelliferyl-β-D-galactoside in DMF diluted, 1:50 in 0.01M sodium phosphate buffer, pH 7.5, containing 0.1M NaCl and 1 mM $MgCl_2$) was added to the wells (100 µl/well), and the resulting fluorescence was measured with a Dynatech MicroFluor plate reader (Dynatech, Alexandria, Va.) using 365 nm as the excitation wavelength and 450 mn as the emission wavelength.

In addition to the samples, standard curves of IgG and PAP dilutions were prepared, and a linear regression analysis was performed. The standards demonstrated a linear response in fluorescence to PAP and IgG concentration as confirmed by the linear regression analysis. From the standard curves, the concentration of PAP or IgG in each fraction was calculated.

The linear regression analysis showed that 44% of the PAP loaded on the column were bound to the column. The amount of monomeric IgG bound to the column was 4.4% of the total IgG loaded on the column. See Table 1 below. These results show that the column was not binding a significant amount of monomeric IgG and was specifically binding immune complexes.

Clearly, there was a large discrepancy between the results of the peroxidase assay (about 5% binding of immune complexes) and the enzyme immunoassay for immunoglobulin (about 44% binding of immune complexes). Closer examination of the kinetics of the two enzymatic reactions revealed that the peroxidase assay reached its maximal absorbance in 5–10 minutes on average, while the streptavidin-β-galactosidase assay reached its maximal fluorescence in 25–30 minutes. Therefore, although the two assays both gave linear responses to incremental increases in concentration of PAP, the enzyme immunoassay measured the relative quantities of PAP more accurately and sensitively due to the longer incubation time.

As a result of the comparison of the results of the peroxidase assay and enzyme immunoassay, elution profiles were reassessed using the enzyme immunoassay. Also, PAP complexes were loaded onto and eluted from the control LHRH and No peptide columns in the same manner as described above for the CBP2 column and assayed using the enzyme immunoassay. The results are shown in Table 1 below.

TABLE 1

| | Percent Bound to Column | | |
|---|---|---|---|
| Sample | CBP2 Column | LRHR Column | No Peptide Column |
| PAP | 44 | 4.8 | 8 |
| Monomeric Rabbit IgG | 4.4 | N.D.* | N.D.* |

*Not Determined

The immune complex binding efficiency of the CBP2 column as shown in Table 1 was much higher than had been previously calculated using the peroxidase assay. The results also indicated that the column specifically bound immune complexes. There was very little binding of the immune complexes to the control LHRH and No peptide columns, showing that the binding of immune complexes was not due to nonspecific binding effects.

C. Elution With CBP2

If PAP binding was a specific interaction between the solid phase CBP2 and the immunoglobulins of PAP, then PAP bound by the column should be eluted using a solution of CBP2, and a solution of a control peptide (LHRH) should cause no elution of bound PAP. This was exactly what was found by the following experiment.

A 1 ml sample of 20 µg/ml PAP was loaded on an equilibrated CBP2 column (prepared as described in Example 3) and allowed to circulate continuously for 15 min over the column. The column was then washed with 12 ml C1q buffer, followed by 3 ml of 336.2 µg/ml CBP2 (this CBP2 concentration was 20 times the concentration of CBP2 needed to give 50% inhibition Ig-HRP binding to C1q) diluted in C1q buffer. An additional 6 ml of C1q buffer was used to wash the column followed by 3 ml of 2% (v/v) acetic acid and then with 6 ml of C1q buffer to completely wash the column. Fractions were collected and assayed for the presence of peroxidase activity as described above in Part A. A control column was run as described above, except that 3 ml of LHRH at an equimolar concentration as the CBP2 solution, was substituted for the CBP2 wash.

Figure 9A:
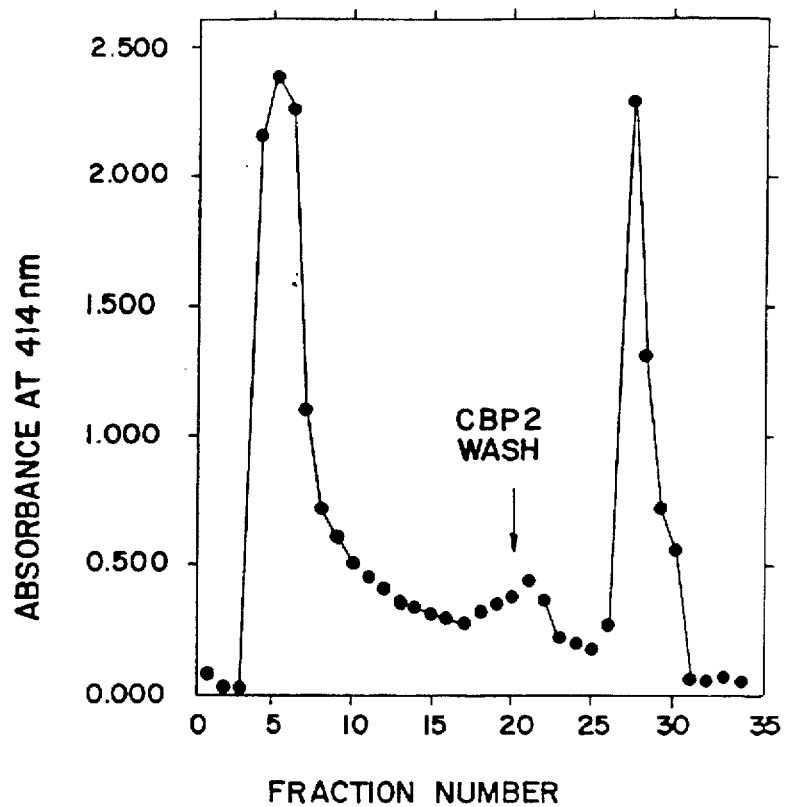
FIG. 9A: Elution of PAP on a CBP2 column washed with solution of CBP2.
Figure 9B:
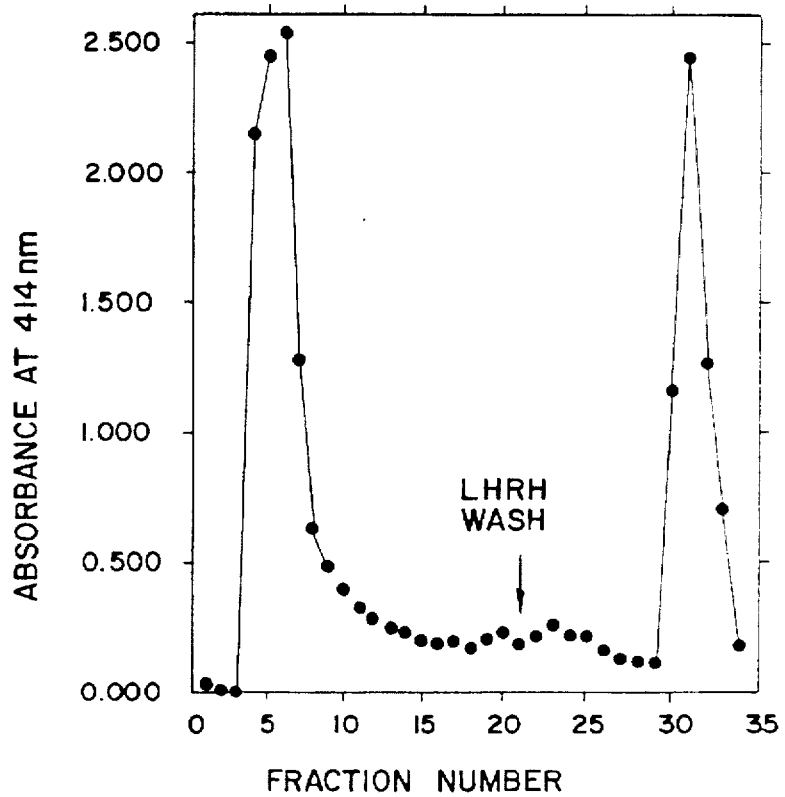
FIG. 9B: Elution profile of PAP on a CBP2 column washed with a solution of LHRH.

As shown in FIG. 9A, the normal flow-through peak was observed, followed by a small but significant PAP peak which was eluted from the column with CBP2. The remaining PAP were eluted by the acetic acid/C1q buffer wash. When the experiment was repeated with LHRH at an equimolar concentration, there was no significant elution of PAP due to the LHRH wash (see FIG. 9B). These results show that PAP binding to the column was dependent on CBP2.

D. Controls

1. The low efficiency of PAP elution by the CBP2 solution could have been explained by either: 1) the presence of inactive CBP2 aggregates effectively lowering the free CBP2 concentration; or 2) because the PAP elution occurred under nonequilibrium conditions. Under nonequilibrium conditions, the CBP2 peptide would not adequately compete with the solid phase CBP2 for binding sites on the PAP since a high affinity interaction (i.e., a functional affinity) between the solid phase CBP2 and the bound PAP had been established.

To address the question of nonequilibrium conditions, a 1 ml sample of 20 µg/ml PAP plus 200 µg/ml CBP2 (0.1 mM; a ten times greater concentration than that required to give 50% inhibition of Ig-HRP binding to C1q) or 152 µg/ml LHRH (0.1mM) was incubated for 1 hour at 25° C. and then loaded on a pre-equilibrated CBP2 column and allowed to pass continuously over the column for 15 min. The sample was then eluted with 21 ml C1q buffer followed by 3 ml of 2% (v/v) acetic acid and then 6 ml C1q buffer. The column fractions were assayed for the presence of peroxidase as described above in Part A, and the concentration of PAP was calculated from the standard curve data.

Figure 10:
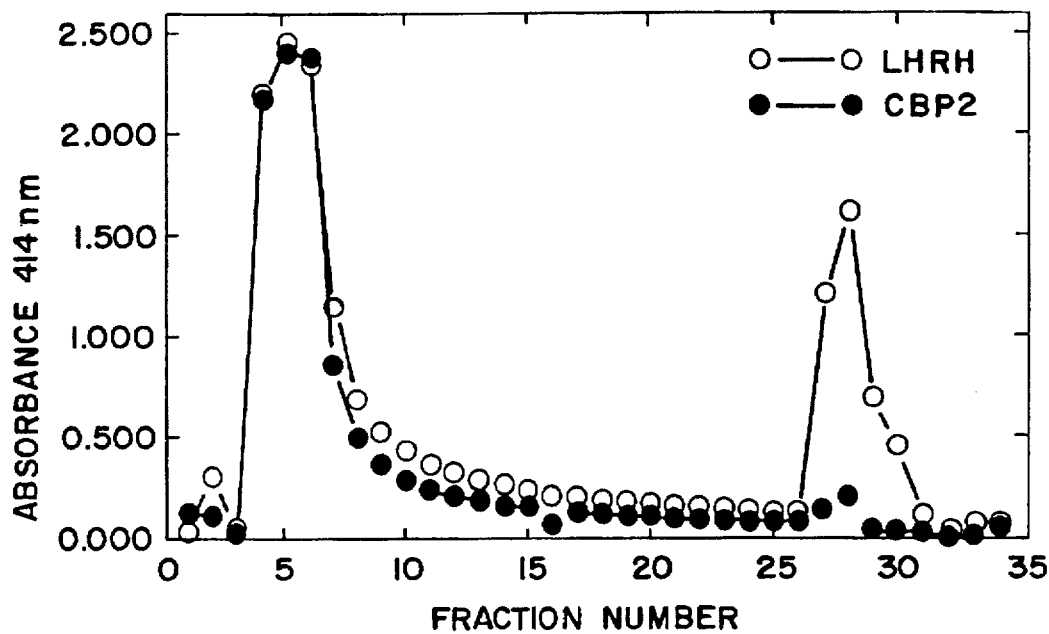
FIG. 10: The elution profile of PAP on the HiPAC™ LTQ-CBP2 column when PAP were incubated with either CBP2 or LHRH prior to being loaded on the column.

The resulting elution profiles are presented in FIG. 10. The sample containing CBP2 and PAP exhibited a dramatic loss of PAP binding to solid phase CBP2 on the column, while the sample containing LHRH and PAP showed PAP binding to the column in the range normally observed. These data show that PAP binding was dependent on CBP2.

If inactive CBP2 aggregates caused the low efficiency of PAP elution, then the same aggregates would effectively reduce the CBP2 concentration and the inhibition of PAP binding in the pre-incubation studies would require very high CBP2 concentrations. This was not the case, however, since similar concentrations were used for column elution as for the pre-incubation studies. Also, another attempt at PAP inhibition in the pre-incubation studies using 156 µg/ml CBP2 demonstrated inhibition of PAP binding (approximately 40%). Thus, the effect of aggregates, if they formed, was of little significance.

2. In order to address the possible effects of acetic acid exposure on PAP, a 20 µg/ml sample of PAP was dissolved in either 2% (v/v) acetic acid or C1q buffer and incubated for 3 hours. Aliquots from both samples were then assayed for peroxidase activity. No significant differences in the two samples were observed. Therefore, an adverse effect of acetic acid on HRP did not account for the results.

3. Although the data indicated that PAP binding was specific and dependent on CBP2, the PAP binding could have been due to a nonspecific interaction of the column with the horseradish peroxidase (HRP) of PAP. Thus, a solution of HRP in C1q buffer was loaded, eluted and assayed for peroxidase as described for the PAP experiments. The linear regression calculations of the resulting profile indicated no significant binding of HRP (only about 7%) to the CBP2 column.

4. The extent of nonspecific binding of PAP to the HiPAC™ matrix was determined. Control columns coupled with either LHRH or No peptide were used in place of the CBP2, in order to assess the extent of nonspecific binding.

In the same manner as described for the CBP2 column, PAP were loaded and eluted either from the LHRH or No peptide column. The column fractions were assayed for the presence of immunoglobulin using the enzyme immunoassay described above in Part B. Linear regression analysis of the standard curves allowed the calculation of the amount of material in the flow-through and acid-eluted fractions.

The results are shown in Table 1 above. The LHRH column bound 4.8% of the total PAP loaded on the column, while the No-peptide column bound 8% of the total PAP. Therefore, the nonspecific binding of PAP to the CBP2 column can account for, at most, a small fraction of the total PAP binding observed.

E. Conclusion

The data show that the binding of PAP to the CBP2 column was specific for immune complexes and dependent on CBP2, and that CBP2 was interacting with the immunoglobulin components of the PAP complex.

Example 5

Aggregated Human IgG Binding to the CBP2 Column

Human IgG was aggregated with alkali according to the method of Jones et al., *J. Immunol. Meth.*, 53, 201–208 (1982). Alkali-aggregated IgG possesses C1q binding activities similar to those of native immune complexes, thereby satisfying the essential criterion for immune complex models.

A 1 ml sample of 100 µg/ml of the aggregated IgG diluted in C1q buffer was loaded onto a CBP2 column (prepared as described in Example 3) that had been equilibrated with 3 ml C1q buffer. The sample was circulated through the column for 15 min and then eluted with 21 ml C1q buffer, followed by 3 ml 2% (v/v) acetic acid, and then by 6 ml C1q buffer.

The fractions were assayed for immunoglobulin by placing duplicate 50 µl aliquots from each fraction and 50 µl of coating buffer into the wells of a microtiter plate and incubating the plate 2 hours at 37° C. The uncoated surfaces were blocked by adding 340 µl/well of PBSC followed by incubation of the plate for 1 hour at 37° C. Next, the wells were washed 3 times with PBSCT. Goat anti-human IgG (Heavy and Light chain specific) F(ab')$_2$ fragments labeled with horseradish peroxidase (Organon Teknika/Cappel, West Chester, Pa.) was added to the wells (100 µl/well) at a 1:30,000 dilution in PBSCT, and the plate was incubated for 2 hours at 25° C. The wells were washed 3 times with PBSCT, OPD substrate buffer added (100 µl/well), and the resultant colored product was measured at 414 nm with a Titertek Multiskan plate reader. A standard curve using a portion of the sample loaded on the column was used in the assay in order to quantitate the amount of IgG in each column fraction.

Figure 11:
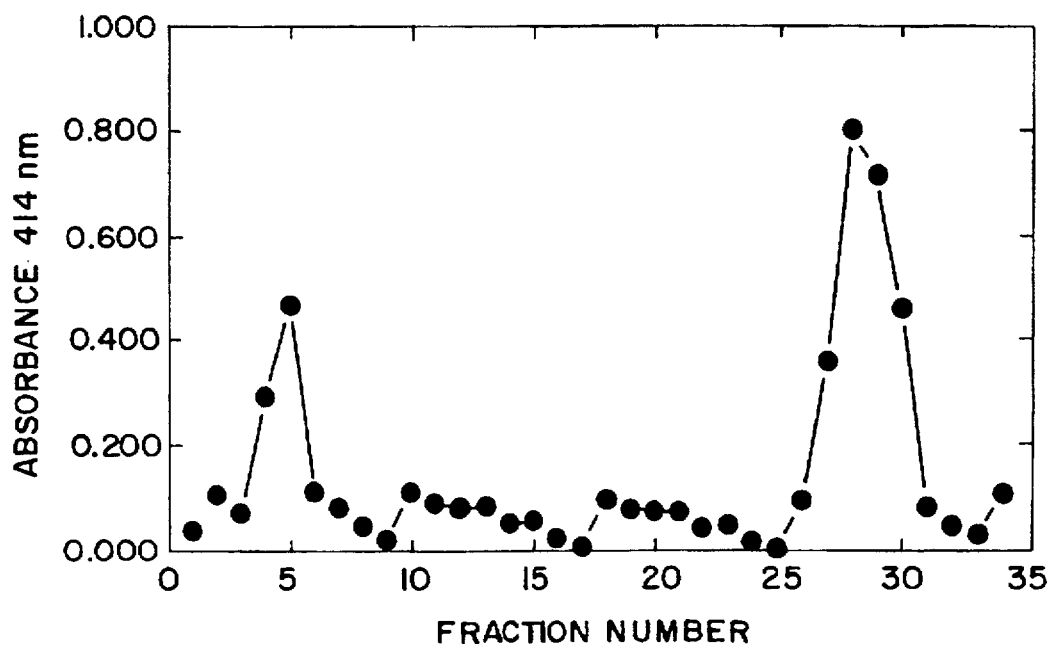
FIG. 11: The elution profile of aggregated human IgG on the HiPAC™ LTQ-CBP2 column.

The elution profile for the aggregated IgG showed two major peaks (FIG. 11). The aggregates not bound by the column were readily eluted with C1q buffer and were found to make up the first, flow-through peak. The flow-through material was calculated to comprise 5% of the total aggregated IgG added to the column. The aggregates bound to the column were eluted with the acetic acid wash and constituted the larger second peak (FIG. 11). Linear regression calculations indicated that 95% of the aggregated IgG loaded on the column was bound to the column and eluted with the acetic acid wash. Based on these data, the efficiency of the CBP2 column for binding aggregated IgG was considered quite high.

Figure 12:
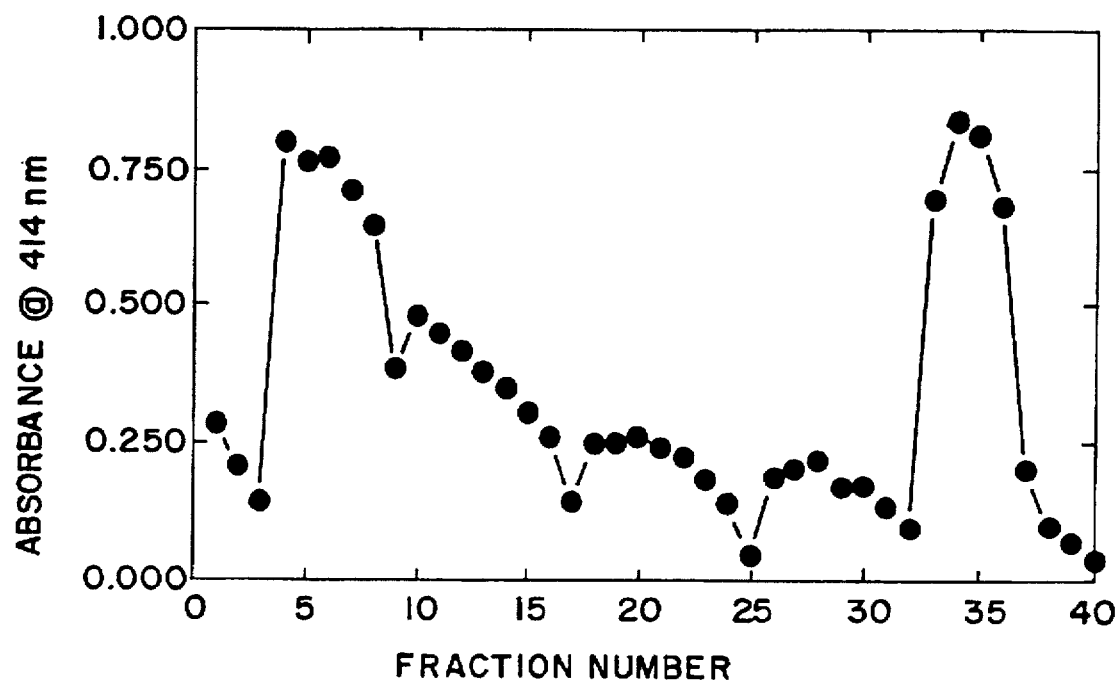
FIG. 12: The elution profile of aggregated human IgG plus monomeric human IgG.

Next, a 1 ml sample of 400 µg/ml monomeric human IgG was diluted in C1q buffer, loaded on a CBP2 column, eluted and assayed in the same fashion as described above for the aggregated human IgG. Also, a one ml sample containing a mixture of 100 µg/ml aggregated human IgG and 400 µg/ml monomeric human IgG in C1q buffer was loaded, eluted, and assayed as described above. The results are shown in FIG. 12 and Table 2 below.

TABLE 2

| | Percent of Added Material Bound to the Column | | |
|---|---|---|---|
| Sample | CBP2 Column | LHRH Column | No Peptide Column |
| Aggregated IgG | 96.7 | 18.8 | 26.3 |
| Monomeric IgG | 31 | N.D.[a] | N.D.[a] |
| Aggregated + Monomeric IgG | 95.9[b] | N.D.[a] | N.D.[a] |

[a]Not Determined
[b]The value shown is the percentage of aggregated IgG bound. The aggregates were biotinylated allowing for a separate determination (see below).

The linear regression analysis calculations indicated that approximately 31% of the total monomeric IgG loaded on the column was bound (see Table 2). This amount of binding of the human monomeric IgG was quite high relative to previous binding experiments using monomeric rabbit IgG. However, there was a significant difference in the amount of binding of aggregated IgG and that of monomeric IgG.

The linear regression calculations for the mixture of aggregated and monomeric human IgG determined that there were 100 µg of IgG in the acid-eluted fractions, indicating that the column bound almost all of the aggregated IgG. Although the calculated amount of IgG in the acid-eluted fractions closely corresponded to the amount of aggregated IgG loaded onto the column, there was no evidence indicating whether or not the aggregated IgG was actually the species binding to the column. It was, therefore, necessary to be able to distinguish the aggregated IgG in a mixture of monomeric IgG and aggregates.

To do this, a 5 mg/ml preparation of aggregated human IgG was labeled with sulfosuccinimididyl-6-(biotin-amido) hexanoate (NHS-LC-Biotin, Pierce Chemical Co., Rockford, Ill.) according to the method of Geudson et al., *J. Histochem. Cytochem.*, 27, 1131–39 (1979). The aggregated IgG had 14% of the available primary amines biotinylated as determined by the 2,4,6-trinitrobenzene sulfonic acid (TNBS) method described in Fields, *Meth. Enzymol.*, 25B, 464–68 (1972). Biotinylation of the aggregates using an N-hydroxysuccinamide ester adduct of biotin allowed the rapid and specific labeling of the aggregates. Biotinylation has been demonstrated to have minimal effects on the native conformations and activities of biomolecules, and CBP2±biotin showed no difference in its Protein A inhibitory activity. In addition, the avidin-biotin interaction is of a very high affinity (femptomolar in magnitude) providing a highly specific and extremely sensitive label for the aggregated IgG.

Next, a 1 ml sample containing biotinylated aggregated human IgG at 100 µg/ml plus monomeric IgG at 400 µg/ml in C1q buffer was loaded, eluted, and the column fractions assayed for immunoglobulin as described above. The fractions were also assayed for biotinylated aggregates as follows. Duplicate 50 µl aliquots of each column fraction were mixed with 50 µl coating buffer in the wells of a microtiter plate, and the plate was incubated for 2 hours at 37° C. The uncoated surfaces of the wells were blocked with PBSC. Avidin plus biotinylated horseradish peroxidase (Vector Laboratories, Inc., Burlingame, Calif.) (5 µl of each) diluted in 1 ml PBSCT were incubated for 30 min at 25° C. and then diluted 1:15 in PBSCT prior to adding 100 µl/well of the resulting complexes to the plate. The plate was incubated for 2 hours at 25° C., the wells washed 3 times with PBSCT, and OPD substrate buffer added, and the colored product measured at 414 nm in a Titertek Multiskan plate reader.

Figure 13A:
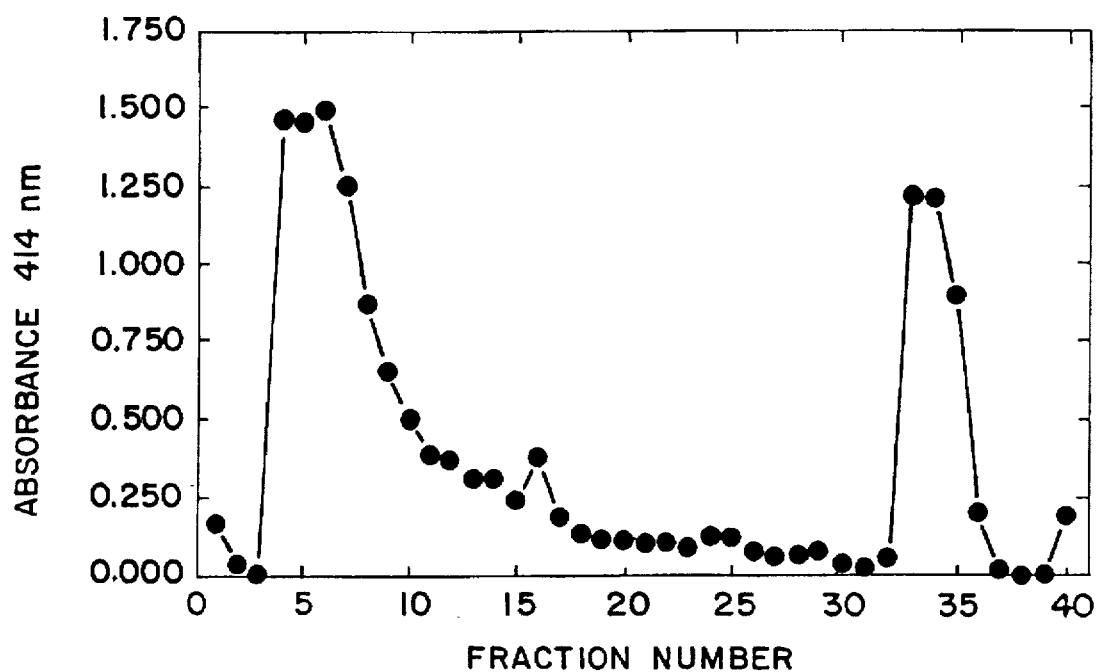
FIG. 13A: The elution profile of biotinylated aggregated human IgG plus monomeric human IgG (total IgG).
Figure 13B:
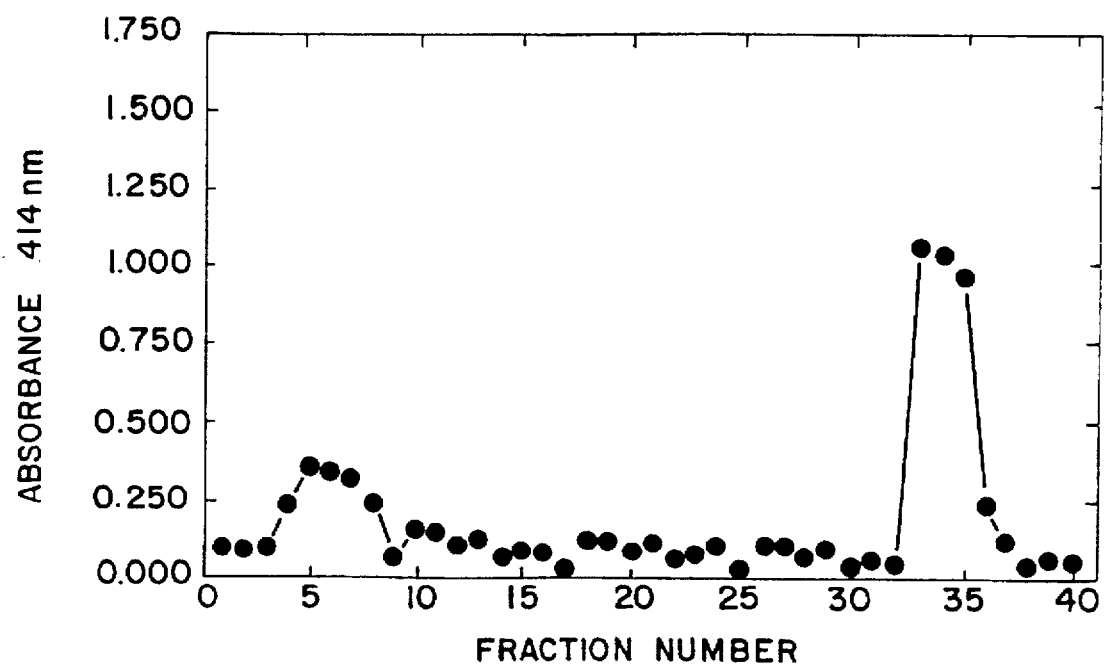
FIG. 13B: The elution profile of biotinylated aggregated human IgG.

The results are shown in FIGS. 13A (assay for immunoglobulin) and 13B (assay for biotinylated aggregated IgG) and Table 2 above. The concentration of biotinylated aggregated IgG was calculated from the standard curve and linear regression analysis, and it was found that 95.6% of the biotinylated aggregated IgG loaded on the column was bound by the column (see Table 2), which indicates that immune complexes can be bound to the CBP2 column specifically in the presence of monomeric immunoglobulin.

As a control, C1q was coated on the wells of a microtiter plate as described in Example 2, and aliquots from each column fraction were incubated with the solid phase C1q for 2 hours at 25° C. The wells were washed 3 times with C1q buffer. Bound immune complexes were assayed as described above using goat anti-human IgG F(ab')$_2$ fragments. Such antibody fragments cannot be bound by C1q, since the fragments have no Fc region.

Figure 13C:
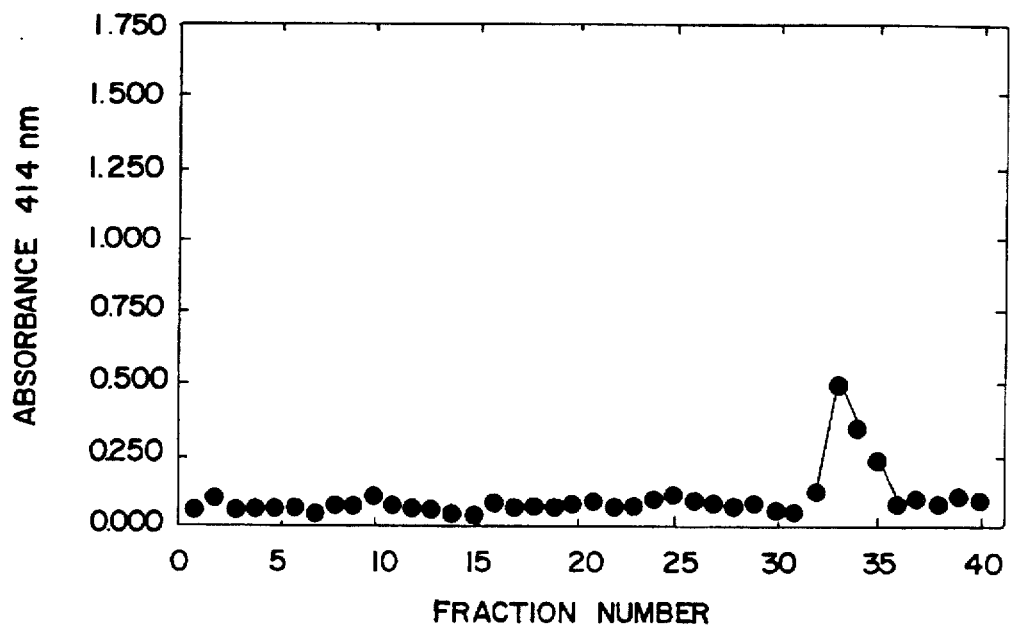
FIG. 13C: The elution profile of C1q binding material.

The results of this assay of C1q binding activity showed that all of the C1q binding material was in the acid-eluted fractions, which are the fractions containing aggregated IgG that bound to the CBP2 column (see FIG. 13C). The combined data show that the CBP2 column can bind human immune complexes specifically, and that the CBP2 column binds immune complexes which are bound by C1q.

The binding of aggregated IgG by the control columns is also shown in Table 2. Approximately 19% of the total aggregates added to the LHRH column were bound to it, while approximately 26% of the total aggregates bound to the No-peptide column. Although the nonspecific binding of the aggregate to the matrix is 19–26%, the binding of aggregated IgG to the CBP2 column (95% of total aggregated IgG) clearly cannot be explained by nonspecific effects alone. Based on the relatively high percentage of nonspecific binding to the matrix, the monomeric IgG binding to the column may be attributable to nonspecific binding.

In conclusion, the above data show that the CBP2 column binds immune complexes that are also bound by C1q and that the CBP2 column is binding immune complexes in a specific fashion.

Example 6

Binding of Aggregated IgG and Serum Components to the CBP2 Column

Figure 14A:
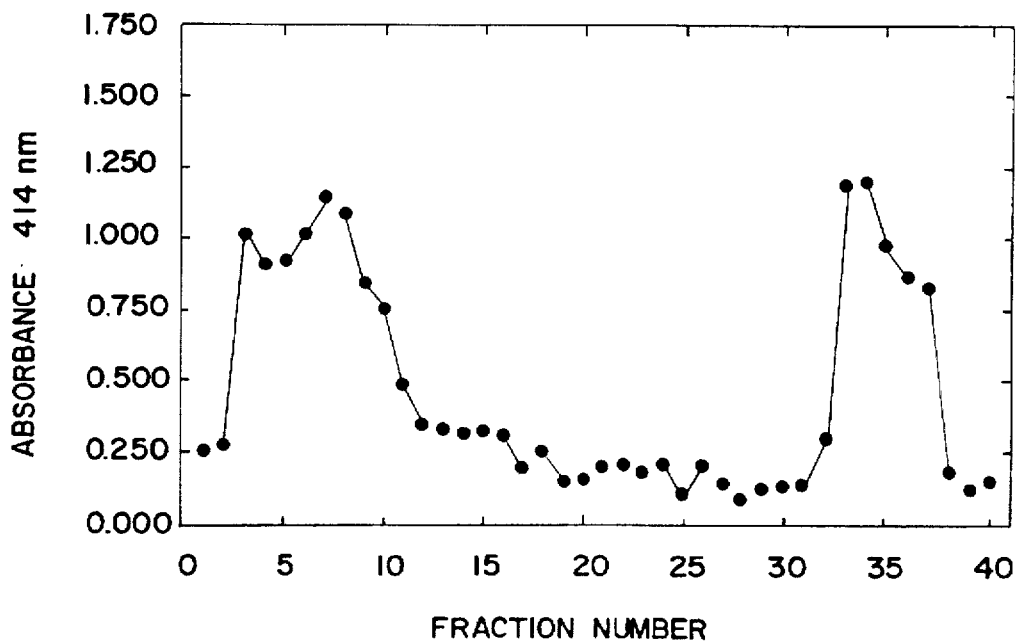
FIG. 14A: The elution profile of biotinylated aggregated human IgG in diluted pooled normal human plasma (total IgG).
Figure 14B:
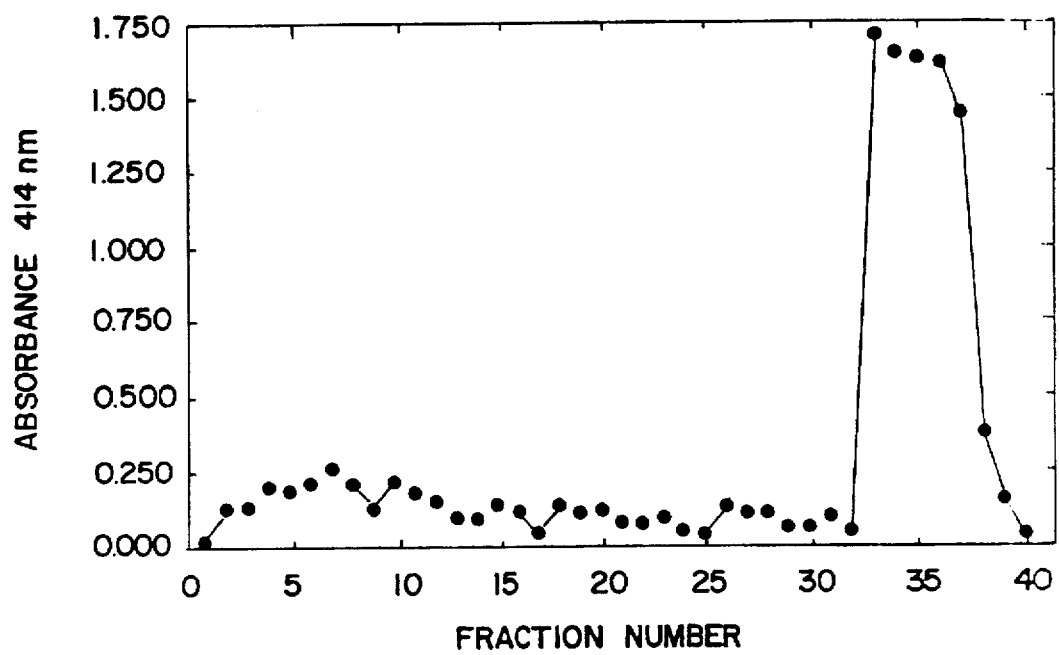
FIG. 14B: Elution profile of aggregated IgG.
Figure 14C:
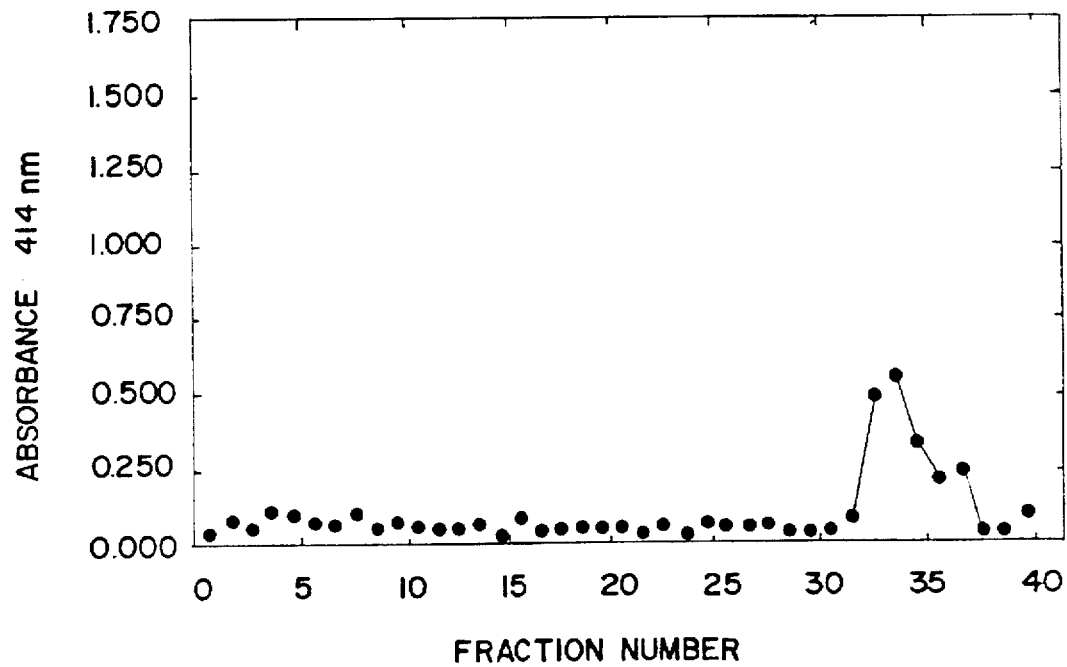
FIG. 14C: Elution profile of C1q binding material.

Biotinylated aggregated IgG (100 µg/ml), prepared as described in Example 5, was diluted in normal human plasma which had been diluted 1:20 with C1q buffer. A 1 ml sample of the aggregated IgG in diluted human plasma was applied to a CBP2 column (prepared as described in Example 3) and eluted with C1q buffer, followed by a 2% (v/v) acetic acid wash to elute the bound material. The column fractions were assayed for immunoglobulin using goat anti-human IgG F(ab')$_2$ as described in Example 5, and the results are shown in FIG. 14A. The biotinylated aggregated IgG was detected with avidin-biotinylated-HRP complexes as described in Example 5, and the results are shown in FIG. 14B. Finally, C1q binding activity was assessed as described in Example 5, and the results are shown in FIG. 14C.

Nearly all of the biotinylated aggregates bound to the column as can be seen in FIGS. 14B and C. The calculated total aggregates bound was 98.2% of the amount added as determined from the linear regression analysis of the accompanying standard curve. Thus, the efficiency of immune complex binding in dilute plasma was quite high.

In view of the success of this experiment, human serum samples were tested on the CBP2 column. The levels of immunoglobulin and immune complexes in the sera were determined prior to their passage over the CBP2 column to establish baseline readings. To do so, either Protein A or C1q was coated on the wells of a microtiter plate as described in Example 2, and then 1:100 diluted serum samples were incubated with the solid phase Protein A or C1q. Any bound material was detected using goat anti-human IgG F(ab')$_2$ fragments labeled with HRP as described in Example 5. A standard curve of aggregated IgG was also included with each assay and provided a way to normalize readings between the two assays (i.e., in aggregated IgG equivalents).

Figure 15:
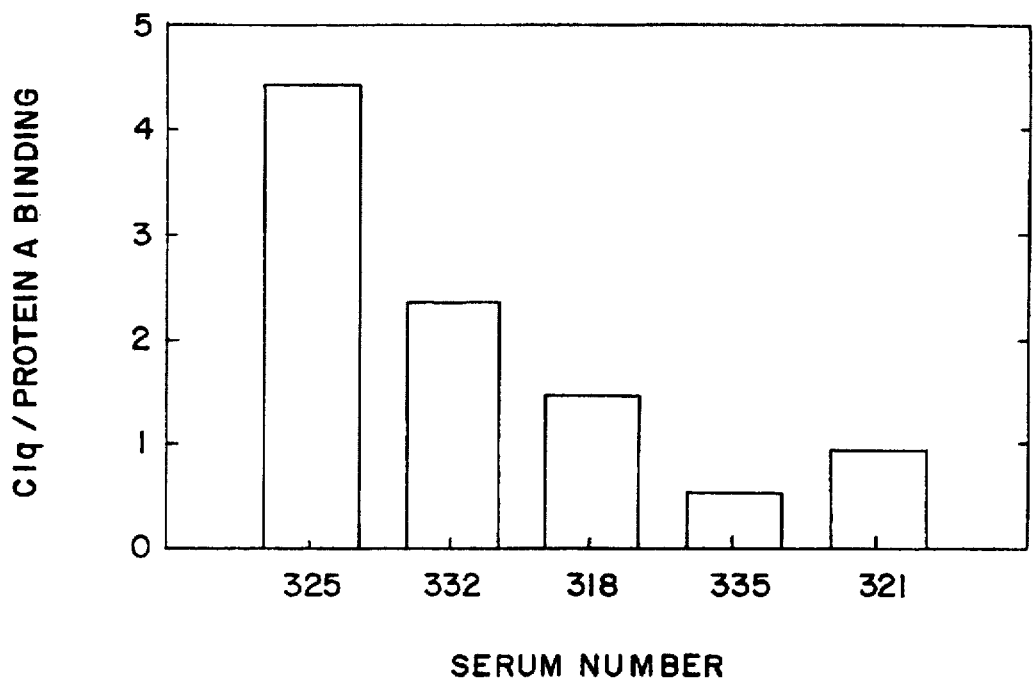
FIG. 15: Graph of the ratio of C1q binding material to Protein A binding material for five patient sera prior to passage over the HiPAC™ LTQ-CBP2 column.

The calculated aggregated IgG equivalents for both the Protein A and C1q assays of the serum samples before passage over the column are presented in Table 3. Ratios of the amounts of material bound by C1q to the amounts of material bound by Protein A, and expressed as percentages, are presented in FIG. 15. The Protein A assay showed that the sera had concentrations of immunoglobulin (IgG) ranging from 726.9 to 1336.2 µg/ml, while the corresponding C1q assay showed immune complex (IC) levels ranged from 7.1 to 32.1 µg/ml (see Table 3).

TABLE 3

Amounts of IgG or Immune Complexes (IC) determined by assay (µg/ml)

| Serum Number | Protein A (IgG) | C1q (IC) |
|---|---|---|
| 325 | 725.9 | 32.1 |
| 332 | 749.1 | 17.6 |
| 318 | 1183.1 | 17.3 |
| 335 | 1336.2 | 7.1 |
| 321 | 1175.7 | 11.0 |

Next, the serum samples were diluted 1:20 with C1q buffer and loaded onto a CBP2 column. The column was washed with C1q buffer, and the bound material eluted from the column with 2% (v/v) acetic acid. The column fractions were assayed for immunoglobulin as described in Example 5. From the resulting elution profiles and the linear regression analysis of the standard curves, the amount of immunoglobulin passed over the column (total IgG) and the amount of material bound (acid-eluted fractions) were determined, and the results are presented in Table 4.

TABLE 4

Amounts of IgG (µg)

| Serum Number | Total IgG Calculated[1] | Total IgG Actual[2] | Acid-Eluted Fractions Calculated[1] | Acid-Eluted Fractions Actual[2] |
|---|---|---|---|---|
| 325 | 36.3 | 126.8 | 1.61 | 4.73 |
| 332 | 37.5 | 49.4 | 0.88 | 2.87 |
| 318 | 59.2 | 33.3 | 0.87 | 1.72 |

TABLE 4-continued

| | Amounts of IgG (μg) | | | |
|---|---|---|---|---|
| | Total IgG | | Acid-Eluted Fractions | |
| Serum Number | Calculated[1] | Actual[2] | Calculated[1] | Actual[2] |
| 335 | 66.8 | 84.77 | 0.36 | 5.08 |
| 321 | 58.8 | 40.5 | 0.55 | 4.59 |

[1]Calculated amount in serum before it was passed over the column using Protein A and C1q binding assays.
[2]Calculated in the present experiment using the assay for IgG.

To the acid-eluted fractions, 100 μl of 3.4M NaOH was added to neutralize the acetic acid. The column fractions were then divided into two groups (the flow-through and the acid-eluted fractions), pooled and then dialyzed against PBS overnight at 4° C. The dialyzed fractions were then aliquoted and stored at −70° C. until the samples could be analyzed as described below.

First, a 1 μg/ml solution of Protein A in coating buffer was incubated in the wells of a microtiter plate (100 μl/well) for 2 hours at 25° C. The uncoated surfaces were blocked with PBSC as described in Example 2. Aliquots (100 μl/well) of both the acid-eluted and flow-through fractions were incubated with the solid phase adsorbed Protein A for 2 hours at 25° C. The wells were then washed 3 times with PBSCT, and goat anti-human IgG F(ab')$_2$ labeled with horseradish peroxidase diluted 1:30,000 in PBSCT was added (100 μl/well). The plate was incubated for 2 hours at 25° C. The wells were washed 3 times with PBSCT, followed by the addition of OPD substrate buffer. The colored product was measured at 414 nm using a Titertek Multiskan plate reader.

Also, C1q was coated onto the wells of a microtiter plate. A 10 μg/ml solution of C1q in coating buffer was added to the wells of a microtiter plate (100 μl/well), and the plate was incubated for 2 hours at 25° C. The wells were blocked with PBSC as described in Example 2. Samples (100 μl/well) from both the acid-eluted fraction and the flow-through fraction were incubated with the solid phase C1q for 2 hours at 25° C. The wells were washed 3 times with PBSCT, and goat anti-human IgG F(ab')$_2$ was added at a 1:30,000 dilution in PBSCT (100 μl/well), and the plate was incubated for 2 hours at 25° C. PBSCT was used to wash the wells 3 times, OPD substrate buffer added, and the colored product measured at 414 nm in a Titertek Multiskan plate reader.

A standard curve of aggregated human IgG was used for both the C1q and protein A binding assays. The use of a common standard curve facilitated a comparison of the results from the two assays, and results were expressed in aggregated IgG equivalents.

Figure 16:
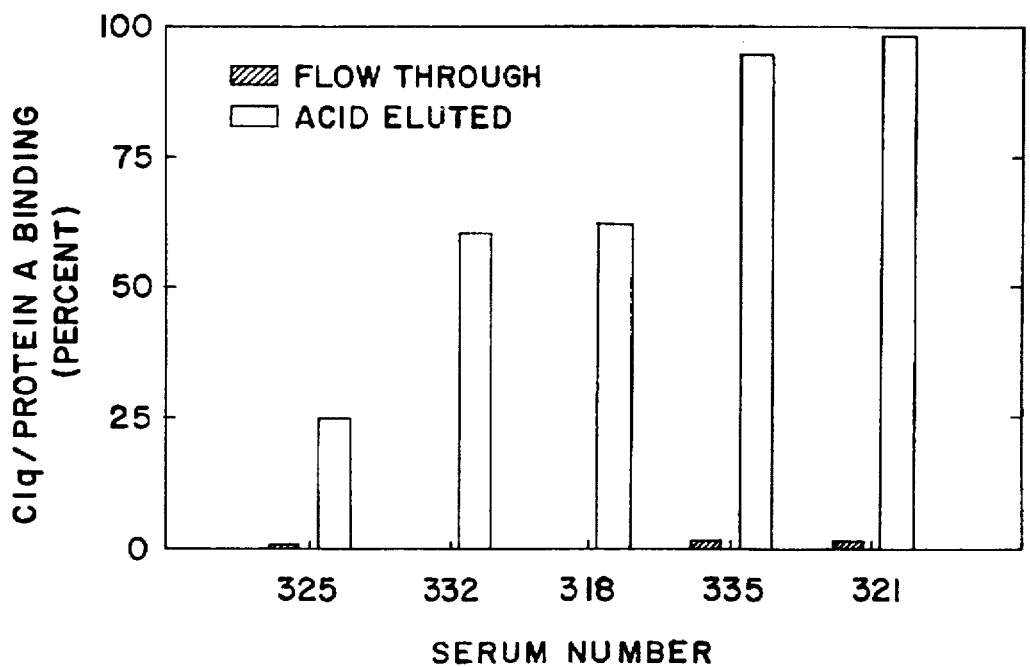
FIG. 16: Graph of the ratio of C1q binding material to Protein A binding material for five patient sera after passage over the HiPAC™ LTQ-CBP2 column.

The amounts of immunoglobulin (Protein A binding material) and immune complexes (C1q binding material), expressed in aggregated IgG equivalents are presented in Table 5. Also, the amount of immune complexes as a percentage of total immunoglobulin is presented in FIG. 16.

TABLE 5

| | Amounts of IgG or Immune Complexes (IC) in Column Fractions (μg/ml) | | | |
|---|---|---|---|---|
| | Flow-Through | | Acid-Eluted | |
| Serum Number | Protein A (IgG) | C1q (IC) | Protein A (IgG) | C1q (IC) |
| 325 | 39.6 | 0.10 | 0.30 | 0.074 |
| 332 | 25.6 | 0.082 | 0.16 | 0.095 |
| 318 | 123.1 | 0.11 | 0.16 | 0.097 |
| 335 | 19.7 | 0.27 | 0.14 | 0.13 |
| 321 | 15.7 | 0.23 | 0.161 | 0.159 |

The C1q binding activity detected in the flow-through fractions was a small percentage of the total IgG as determined by Protein A binding (Table 5). The acid-eluted fractions had a much higher percentage of C1q binding material when compared to the Protein A reactive material (Table 5). In some cases it was as high as 98%. By comparing the results presented in FIG. 16 with the results in FIG. 15, it can be seen that the acid-eluted fractions were enriched with immune complexes (as detected by the C1q assay).

The efficiency of the column [the ratio of the total amount of C1q bound material in the pooled acid-eluted fractions versus the amount of C1q binding material in a 1 ml sample of 1:20 diluted serum before passage over the column] ranged widely from 23% to 109%. This variability may be due to the fact that sera vary in their immune complex content due to the variation from person to person. The CBP2 column and the C1q assay may also be detecting different species of immune complexes. C1q has very distinct binding affinities for IgG subclasses and for IgM, but the immunoglobulin specificity of the CBP2 column remains to be determined.

Example 7

HiPAC™ Fast Protein Liquid Chromatography (FPLC) Column

A. CBP2 Coupling to HiPAC™ FPLC Column.

CBP2 was coupled to an HiPAC™ FPLC column (dimensions of 0.6 mm×10 cm) in the following fashion. The column was equilibrated with 10 column volumes (18 ml) of 0.1M sodium citrate, pH 5.5, at a flow rate of 1 ml/min at 25° C. A ligand solution of 1.4 mg/ml CBP2 diluted in 0.1M sodium citrate, pH 5.5, plus 20 mg/ml sodium cyanoborohydride was prepared, and a 3 ml sample applied to the column. The sample was circulated through the column for 20 min at 25° C. at a flow rate of 1 ml/min using a peristaltic pump (Rainin Inc., Woburn, Mass.). The column was then washed with 20 ml of sodium citrate, pH 5.5, at 1 ml/min followed by 10 ml of 2M guanidine-HCl, and then 10 ml of 0.05M Tris, pH 9.0, at the same flow rate. The column was then washed with 20 ml C1q buffer and stored in C1q buffer for future use. This column had a bed volume of 1.8 ml as compared to 0.8 ml for the LTQ column.

The extent of CBP2 coupling to the column was determined by directly assaying the column with Ellman's reagent as described in Example 3. The amount of CBP2 coupled to the column as determined by this assay was 756 μg. The density of CBP2 in relation to the column volume was 420 μg CBP2/ml matrix. This is 20% less than the density obtained for the LTQ column, which was 525 μg CBP2/ml matrix.

B. Aggregated Human IgG Binding to the FPLC-CBP2 Column.

The CBP2/FPLC column was equilibrated with C1q buffer at a flow rate of 1 ml/min for 15 min using a Beckmam HPLC (Model 421 controller and 112 solvent delivery module, Palo Alto, Calif.). A 2 ml sample of 100 μg/ml aggregated human IgG (prepared as described in Example 5) diluted in C1q buffer was loaded onto the column with C1q buffer at a flow rate of 1 ml/min for 2 min. The flow rate was then increased to 2 ml/min, and maintained for 20 minutes, at which time the flow rate was reduced to 1 ml/min. The column was next washed with 2% (v/v) acetic acid at a flow rate of 1 ml/min for 12 min, followed by C1q buffer at a flow rate of 1 ml/min for 6 min. The column eluate was collected at 1 minute intervals and assayed for the presence of immunoglobulin as described in Example 5.

Figure 17:
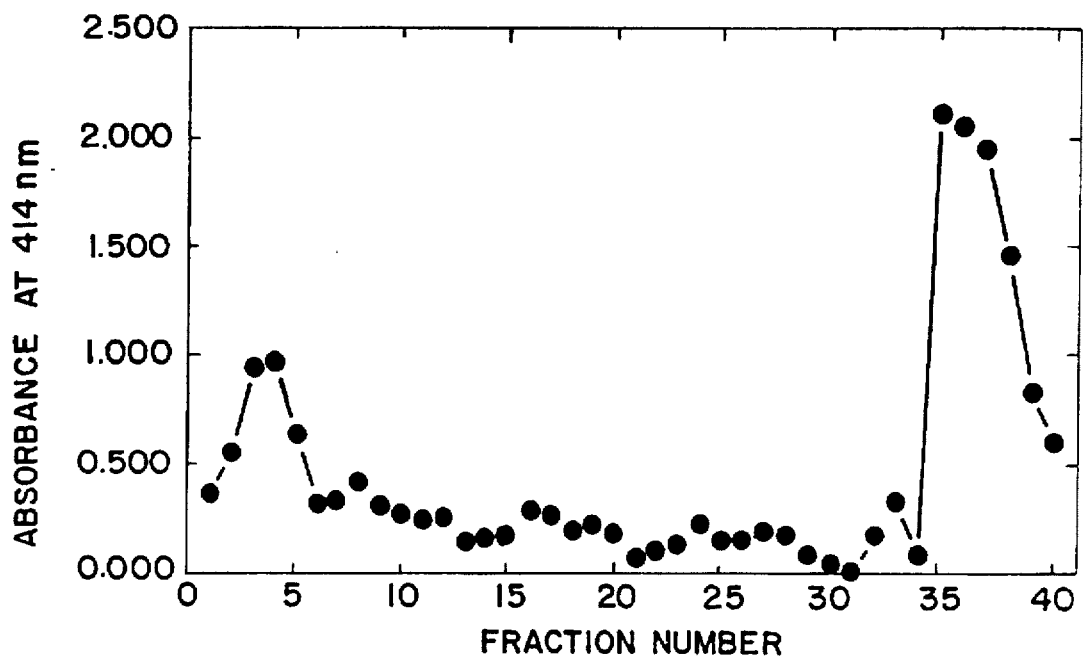
FIG. 17: Shows the elution profile of aggregated human IgG diluted in C1q buffer and passed over the HiPAC™ FPLC-CBP2 column.

The resulting profile is presented in FIG. 17. From the linear regression calculations, the concentration of aggregated IgG in each column fraction was determined. According to the calculations, 96% of the total aggregated IgG added to the column was found in the acid-eluted fractions. Therefore the column was able to bind immune complexes with a high efficiency.

In order to determine the specificity of the FPLC-CBP2 column for immune complexes, monomeric human IgG was loaded and eluted from the column and assayed as described above for the aggregated IgG. The linear regression calculations determined that 13% of the monomeric IgG loaded on the column was bound to the column, indicating that the FPLC-CBP2 column was in fact specific for immune complexes and more specific than the LTQ column which exhibited 31% binding of monomeric human IgG.

Next, biotinylated aggregated IgG at 100 μg/ml was added to human plasma diluted 1:20 in C1q buffer, and a 2 ml aliquot of the sample was loaded and eluted from the CBP2-FPLC column as described above and then assayed for total IgG and biotinylated aggregated IgG as described in Example 6.

Figure 18:
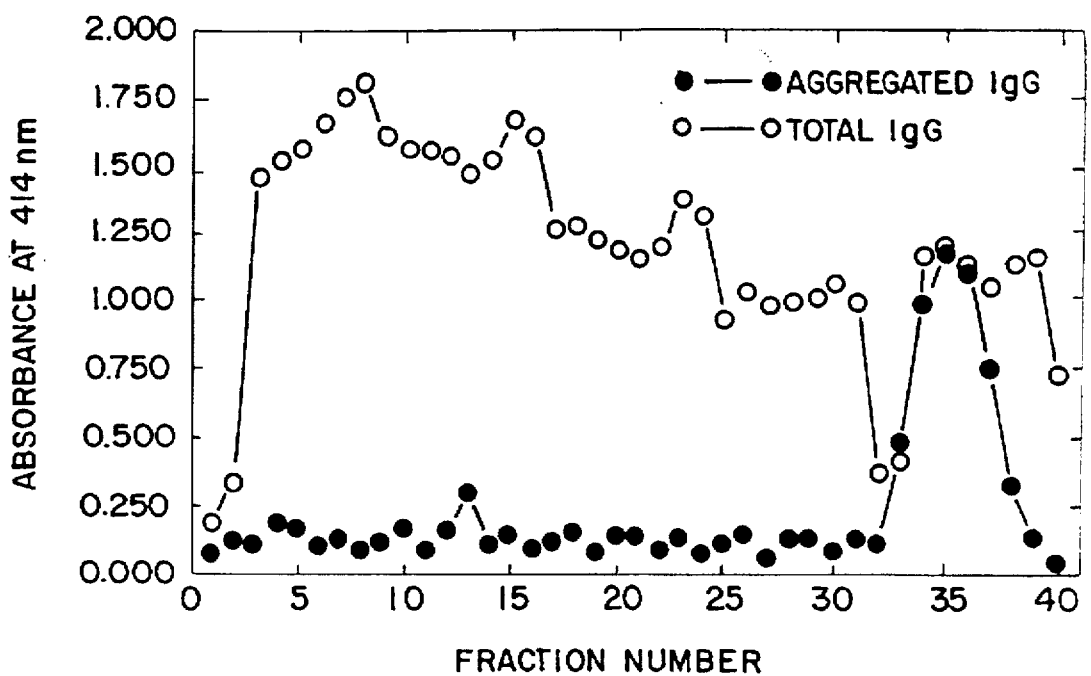
FIG. 18: Shows the elation profile of biotinylated aggregated human IgG diluted in normal human plasma and passed over the HiPAC™ FPLC-CBP2 column.

The resulting profiles are presented in FIG. 18. FIG. 18 shows extensive trailing of the flow-through material, with a drop in IgG concentration prior to the acid-elution fractions. The acid-elution fractions have a peak of IgG. The aggregated IgG profile in FIG. 18 shows that the aggregates remained bound to the column despite extensive flow-through of excess IgG, until they were eluted by the acid wash. Based on linear regression analysis of the aggregated IgG profile, nearly all of the biotinylated aggregated IgG was bound by the column. The data also indicated that the FPLC-CBP2 column could bind immune complexes preferentially in the presence of free monomeric IgG, in a fashion similar to the LTQ-CBP2 column.

C. Human Serum Components Binding to the FPLC-CBP2 Column.

Sera were diluted 1:20 in C1q buffer and loaded and eluted as described above, and the column fractions assayed as described in Example 6. The results are presented in Tables 7 and 8 and FIG. 19.

Figure 19:
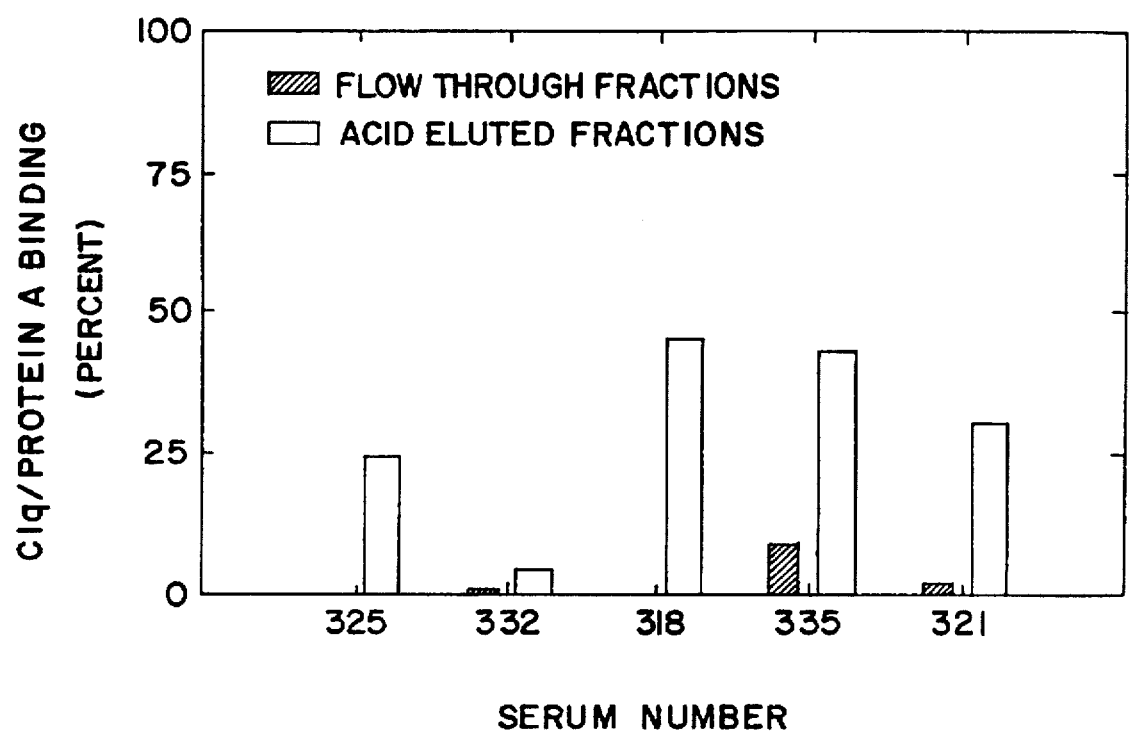
FIG. 19: Graph of the ratio of C1q binding material to Protein A binding material for five patient sera after passage over the HiPAC™ FPLC-CBP2 column.

Table 7 shows the total IgG in the initial serum sample ("calculated"), the total IgG found in the eluted fractions after the serum samples were passed over the column ("actual"), the amount of immune complexes bound to the column and eluted with the acid wash (acid-eluted fractions) ("actual"), and the amount of immune complexes in the initial sample ("calculated"). FIG. 19 shows the ratio of C1q binding material to Protein A binding material for each serum sample based on the values in Table 8 which shows the amounts of Protein A and C1q binding material in the pooled flow-through and acid-eluted fractions.

TABLE 7

| Serum Number | Total IgG (μg) | | Acid-Eluted Fractions (μg) | |
|---|---|---|---|---|
| | Calculated[1] | Actual[2] | Calculated[1] | Actual[2] |
| 325 | 72.6 | 254.5 | 1.76 | 0.376 |
| 332 | 75.0 | 130.8 | 1.76 | 3.86 |
| 318 | 118.2 | 138.62 | 1.74 | 2.33 |
| 335 | 133.6 | 141.64 | 0.72 | 1.71 |
| 321 | 117.6 | 280.79 | 1.10 | 3.02 |

[1]Calculated amount in serum before passage over the column as determined by binding to Protein A or C1q.
[2]Calculated amount in fractions after passage over the column; calculated using assay for IgG.

TABLE 8

| | Amounts of IgG or IC in Column Fractions μg/ml) | | | |
|---|---|---|---|---|
| | Flow-Through | | Acid-Eluted | |
| Serum Number | Protein A Binding (IgG) | C1q Binding (IC) | Protein A Binding (IgG) | C1q Binding (IC) |
| 325 | 83.2 | 0.0795 | 0.188 | 0.0458 |
| 332 | 42.7 | 0.342 | 0.68 | 0.0291 |
| 318 | 73.2 | 0.0867 | 0.497 | 0.224 |
| 335 | 27.0 | 2.45 | 0.270 | 0.116 |
| 321 | 82.9 | 1.45 | 0.584 | 0.178 |

Based on the data, the FPLC-CBP2 column appeared to bind immune complexes in a similar fashion as the LTQ-CBP2 column. The FPLC-CBP2 column, like the LTQ column, also demonstrated a significant enrichment for C1q binding material in the acid-eluted fractions.

The FPLC-CBP2 column efficiencies differed significantly from the LTQ column efficiencies with regards to sera 325 and 332 (Table 9). Both columns demonstrated high binding efficiencies for sera 335 and 321, while serum 318 was bound with a moderate efficiency by both columns.

TABLE 9

| | Efficiency | |
|---|---|---|
| Serum Number | CBP2-LTQ Column | CBP2-FPLC Column |
| 325 | 23% | 8.54% |
| 332 | 54% | 9.94% |
| 318 | 56% | 78.1% |
| 335 | 109% | 96.7% |
| 321 | 87% | 97.2% |

*The efficiency of binding was calculated as the percentage of actual ICs in the acid-eluted fractions over the calculated ICs in the sample added to the column.

In conclusion, based on similar trends in immune complex binding efficiencies and enrichments, the FPLC-CBP2 column was determined to be a reasonable scaled-up version of the LTQ-CBP2 column.

We claim:

1. A method of removing immune complexes or aggregated immunoglobulins from a fluid containing monomeric immunoglobulin comprising:

contacting the fluid with a binding material comprising plural binding peptides, the binding peptides being in sufficient proximity on the binding material so that the binding material selectively binds the immune complexes or aggregated immunoglobulins in the fluid, the binding peptides comprising the sequence:

Leu Glu Gln Gly Glu Asn Val Phe Leu Gln Ala Thr; [SEQ ID NO 2]
1           5                   10 and then separating the fluid from the peptide.

2. The method of claim 1 wherein the peptides have the following sequence:

Leu Glu Gln Gly Glu Asn Val Phe Leu Gln          [SEQ ID NO 3]
1           5                   10
          Ala Thr Leu Leu Cys.
                        15

3. The method of claim 1 wherein the binding material is a solid phase having the binding peptides attached thereto.

4. A device for removing immune complexes or aggregated immunoglobulins from a fluid containing monomeric immunoglobulin comprising:

a binding material comprising plural binding peptides, the binding peptides being in sufficient proximity on the binding material so that the binding material selectively binds the immune complexes or aggregated immunoglobulins in the fluid, the binding peptides comprising the following sequence:

[SEQ ID NO 2]

Leu Glu Gln Gly Glu Asn Val Phe Leu Gln Ala Thr,;
1           5                   10 and a means for encasing the binding material so that the fluid can be contacted with it.

5. The device of claim 4 wherein the peptides have the following sequence:

Leu Glu Gln Gly Glu Asn Val Phe Leu Gln   [SEQ ID NO 3]
1             5                       10
    Ala Thr Leu Leu Cys.
              15

6. The device of claim 4 wherein the binding material is a solid phase having the binding peptides attached thereto.

* * * * *